United States Patent [19]
Li et al.

[11] Patent Number: 5,998,164
[45] Date of Patent: *Dec. 7, 1999

[54] POLYNUCLEOTIDES ENCODING HUMAN G-PROTEIN COUPLED RECEPTOR GPRZ

[75] Inventors: Yi Li, Gaithersburg, Md.; Liang Cao, Monmouth Terrace, The Hong Kong Special Administrative Region of the People's Republic of China; Jian Ni, Gaithersburg, Md.; Reiner Gentz, Silver Spring, Md.; Carol J. Bult, Laurel, Md.; Granger G. Sutton, III, Columbia, Md.; Craig A. Rosen, Laytonsville, Md.

[73] Assignee: Human Genome Sciences, Inc., Rockville, Md.

[ * ] Notice: This patent issued on a continued prosecution application filed under 37 CFR 1.53(d), and is subject to the twenty year patent term provisions of 35 U.S.C. 154(a)(2).

[21] Appl. No.: 08/467,948

[22] Filed: Jun. 6, 1995

Related U.S. Application Data

[63] Continuation-in-part of application No. PCT/US95/04079, Mar. 30, 1995.

[51] Int. Cl.⁶ .............................. C12N 15/12; C12N 15/62
[52] U.S. Cl. .................... 435/69.1; 435/69.7; 435/252.3; 435/320.1; 536/23.4; 536/23.5
[58] Field of Search ................................ 435/69.1, 69.7, 435/252.1, 320.1; 536/23.5, 23.4

[56] References Cited

U.S. PATENT DOCUMENTS

| | | | |
|---|---|---|---|
| 5,053,337 | 10/1991 | Weinshank et al. | 435/240.2 |
| 5,155,218 | 10/1992 | Weinshank et al. | 435/240.2 |
| 5,284,755 | 2/1994 | Gearing et al. | 435/69.1 |

FOREIGN PATENT DOCUMENTS

| | | |
|---|---|---|
| 92/01810 | 2/1992 | WIPO . |
| WO 93/07294 | 4/1993 | WIPO . |
| 94/05695 | 3/1994 | WIPO . |

OTHER PUBLICATIONS

PCT International Search Report.
Raming, K., et al., Nature, 361:353–356 (1993).
Hla, T., et al., The Journal of Biological Chemistry, 265(16):9308–9313 (1990).
Nef, P., et al., PNAS, USA, 89:8948–8952 (1992).
Rohrer, L., et al., PNAS, USA, 90:4196–4200 (1993).
Iwai, N., et al., FEBS, 298(2,3):257–260 (1992).
Libert, F., et al., Science, 244:569–572 (1989).
Kaplan, M., et al., The Journal of Immunology, 151(2):626–636 (1993).
Ross, P., et al., PNAS, USA, 87:3052–3056 (1990).
Peralta, E., et al., The EMBO Journal, 6(13):3923–3929 (1987).
Young, D., et al., PNAS, USA, 85:5339–5342 (1988).
McAllister, G., et al., PNAS, USA, 89:5517–5521 (1992).
Lovenberg, T., et al., Neuron, 11:449–458 (1993).
Amlaiky, N., et al., The Journal of Biological Chemistry, 267(28):19761–19764 (1992).
Foguet, M., et al., The EMBO Journal, 11(9):3481–3487 (1992).
Faà, V. et al., "Mutations in the vasopressin V2–receptor gene in three families of Italian descent with nephrogenic diabetes insipidus," Human Molec. Genetics 3:1685–1686 (Sep. 1994).
Khan, A.S. et al., "Single pass sequencing and physical and genetic mapping of human brain cDNAs," Nature Genetics 2:180–185 (1992).
Lee, N.H. and A.R. Kerlavage, "Molecular Biology of G–Protein–Coupled Receptors," Drug News & Perspectives 6:488–497 (1993).
Oliveira, L. et al., "A common motif in G–protein–coupled seven transmembrane helix receptors," J. Computer–Aided Molec. Design 7:649–658 (1993).
Ressler, K.J. et al., "A Zonal Organization of Odorant Receptor Gene Expression in the Olfactory Epithelium," Cell 73:597–609 (1993).
Toguchida, J. et al., "Complete Genomic Sequence of the Human Retinoblastoma Susceptibility Gene," Genomics 17:535–543 (1993).
NCBI Entrez, GenBank, Accession No. L14566, Ressler, K.J. et al. (Feb. 1994).
NCBI Entrez, GenBank, Accession No. L11910, Toguchida, J. et al. (Nov. 1994).
NCBI Entrez, GenBank, Accession No. L06109, Kaplan, M.H. et al. (Aug. 1996).
Supplementary Partial European Search Report for EP 95 91 5505, mailed May 11, 1999.
NCBI Entrez, GenBank Report, Accession No. D40713, Sasaki, T. et al. (Nov. 1994).
NCBI Entrez, GenBank Report, Accession No. R72182, Hillier, L. et al. (Jun. 1995).
NCBI Entrez, GenBank Report, Accession No. R75681, Hillier, L. et al. (Jun. 1995).
NCBI Entrez, GenBank Report, Accession No. D27917, Kohara, Y. et al. (Nov. 1995).
NCBI Entrez, GenBank Report, Accession No. T02954, Khan, A.S. et al. (1997).
NCBI Entrez, GenBank Report, Accession No. D22621, Sasaki, T. and Y. Minobe (1998).
NCBI Entrez, GenBank Report, Accession No. D22698, Sasaki, T. and Y. Minobe (1998).

Primary Examiner—John Ulm
Attorney, Agent, or Firm—Sterne, Kessler, Goldstein & Fox P.L.L.C.

[57] ABSTRACT

Human G-protein coupled receptor or polypeptides and DNA (RNA) encoding such polypeptides and a procedure for producing such polypeptides by recombinant techniques is disclosed. Also disclosed are methods for utilizing such polypeptides for identifying antagonists and agonists to such polypeptides and methods of using the agonists and antagonists therapeutically to treat conditions related to the under-expression and overexpression of the G-protein coupled receptor polypeptides, respectively. Also disclosed are diagnostic methods for detecting a mutation in the G-protein coupled receptor nucleic acid sequences and an altered level of the soluble form of the receptors.

34 Claims, 18 Drawing Sheets

FIG. 1A

```
        10                    30                    50
GGCACGAGGTCATTCAACATTTATTCAACAAAAATACTAAGTCAGCTCTATACAAACTA
        70                    90                   110
ATGGAAGGATACAGCTATGCAAATATAGAACACTAAAGTGTTACATGACAGATGTATGAG
                                                        M  S
       130                   150                   170
TAGTGAAATGGTGAAAAATCAGACAATGGTCACAGAGTTCCTCCTACTGGGATTTCTCCT
 S  E  M  V  K  N  Q  T  M  V  T  E  F  L  L  L  G  F  L  L
       190                   210                   230
GGGCCCAAGGATTCAGATGCTCCTCTTCTTTGGGCTCTTCTCCCTGTTCTATGTCTTCACCCT
 G  P  R  I  Q  M  L  L  F  L  G  L  F  S  L  F  Y  V  F  T  L
       250                   270                   290
GCTGGGGAATGGGACCATCCTGGGACTCATCTCACTGGACTCCAGACTCCACACCCCCAT
 L  G  N  G  T  I  L  G  L  I  S  L  D  S  R  L  H  T  P  M
       310                   330                   350
GTACTTCTTCCTCTCACACCTGGCCGTCGTCAACATCGCCTATGCCTGCAACACAGTGCC
 Y  F  F  L  S  H  L  A  V  V  N  I  A  Y  A  C  N  T  V  P
       370                   390                   410
CCAGATGCTGGTGAACCTCCTGCATCCAGCCAAGCCCATCTCCTTTGCTGGTTGCATGAC
 Q  M  L  V  N  L  L  H  P  A  K  P  I  S  F  A  G  C  M  T
       430                   450                   470
ACTAGACTTTCTCTTTTTGAGTTTTGCACACATACTGAATGCCTCCCTGTTGGTGCTGATGTC
 L  D  F  L  F  L  S  F  A  H  T  E  C  L  L  L  V  L  M  S
       490                   510                   530
CTACGATCGGTACGTGGCCATCTGCCACCCTCCGATATTTCATCATGACCTGGAA
 Y  D  R  Y  V  A  I  C  H  P  L  R  Y  F  I  M  T  W  K
       550                   570                   590
AGTCTGCATCACTCTGGGCATCACTTCCTGGACATGTGGCTCCCTCCTGGCTATGGTCCA

MATCH WITH FIG. 1B
```

FIG. 1B

MATCH WITH FIG. 1A

```
 V  C  I  T  L  G  I  T  S  W  T  C  G  S  L  L  A  M  V  H
TGTGAGCCTCATCCTAAGACTGCCCTTTGTGGGCCTCGTGAAATCAACCACTTCTCTG
                         630                          650
 V  S  L  I  L  R  L  P  F  C  G  P  R  E  I  N  H  F  F  C
       670                          690                          710
TGAAATCCTGTCTGTCCTCAGGCTGGCCTGTGCTGATACCTGGCTCAACCAGGTGGTCAT
 E  I  L  S  V  R  L  A  C  A  D  T  W  L  N  Q  V  V  I
                          730                          750                          770
CTTTGaAGCCTGCATGTTCATCCTGGTGGGACCACTCTGCCTGGTGCTGGTCTCCTACTC
 F  E  A  C  M  F  I  L  V  G  P  L  C  L  V  L  V  S  Y  S
      790                          810                          830
ACACATCCTGGGGCATCCTGAGGATCCAGTCTGGGGAGGCCCGCAGAAAGGCCTTCTC
 H  I  L  G  G  I  L  R  I  Q  S  G  E  G  R  R  K  A  F  S
      850                          870                          890
CACCTGCTCCTCCCACCTCTGCGTAGTGGGACTCTTCTTTGGSAGCGCCATCGTCATGTA
 T  C  S  S  H  L  C  V  V  G  L  F  F  G  S  A  I  V  M  Y
      910                          930                          950
CATGGCCCCCTAAGTCCCGCCATCCTGAGGAGCAGCAGAAGGTCCtTTTTCtTATTTACA
 M  A  P  K  S  R  H  P  E  E  Q  Q  K  V  L  F  L  I  L  Q
      970                          990                         1010
GTTCcTTTCAACCCCTGATTTACAACCCTGATTTACAACCCTGAGGAATGTAGAGGGT
 F  L  S  T  P  M  L  K  P  P  D  D  L  Q  P  *
      1030                         1050                         1070
CAaGggtGCcCTCCGAGGAGACCActGTGCAARGRAAGTCAtTCCtAAGGGGTGTGACAT
      1090                         1110                         1130
```

MATCH WITH FIG. 1C

FIG. 1C

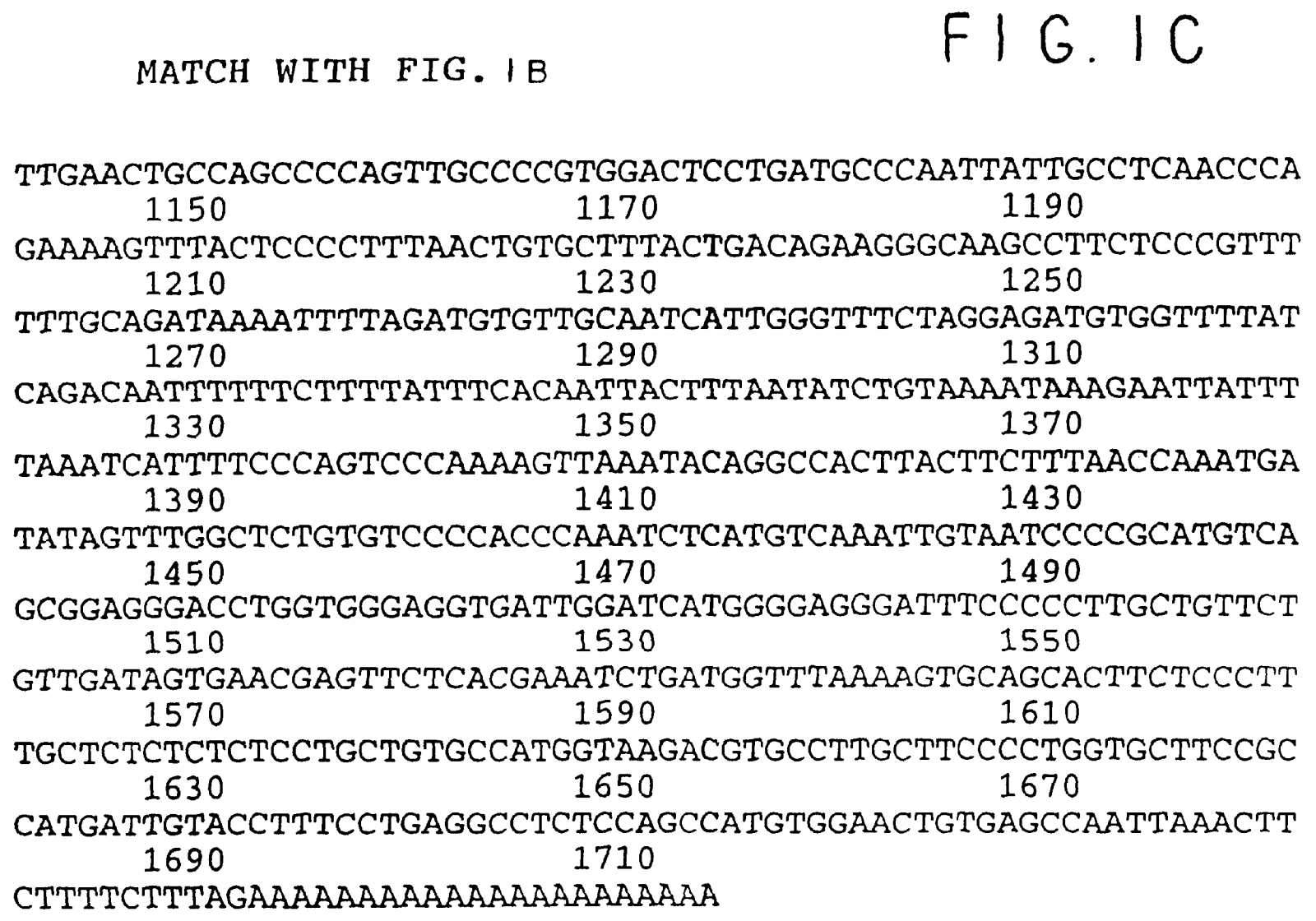

MATCH WITH FIG. 1B

TTGAACTGCCAGCCCCAGTTGCCCCGTGGACTCCTGATGCCCCAATTATTGCCTCAACCCA
          1150                1170                1190
GAAAAGTTACTCCCCTTTAACTGTGCTTTACTGACAGAAGGGCAAGCCTTCTCCCGTTT
          1210                1230                1250
TTTGCAGATAAATTTTAGATGTGTTGCAATCATTGGGTTTCTAGGAGATGTGGTTTTAT
          1270                1290                1310
CAGACAATTTTTCTTTTATTTCACAATTACTTTAATATCTGTAAATAAAGAATTATTT
          1330                1350                1370
TAAATCATTTCCCAGTCCCAAAAGTTAAATACAGGCCACTTACTTCTTTAACCAAATGA
          1390                1410                1430
TATAGTTTGGCTCTGTGTCCCCACCCAAATCTCATGTCAAATTGTAATCCCGCATGTCA
          1450                1470                1490
GCGGAGGGACCTGGTGGGAGGTGATTGGATCATGGGGAGGATTTCCCCTTGCTGTGTCT
          1510                1530                1550
GTTGATAGTGAACGAGTTCTCACGAAATCTGATGGTTTAAAAGTGCAGCACTTCTCCCTT
          1570                1590                1610
TGCTCTCTCTCCCTGCTGTGCCATGGTAAGACGTAAGACGTAAGCTTGCTTCCCCTGGTGCTTCCGC
          1630                1650                1670
CATGATTGTACCTTCCTGAGGCCTCCCAGCCATGTGGAACTGTGAGCCAATTAAACTT
          1690                1710
CTTTTCTTTTAGAAAAAAAAAAAAAAAAAAAA

FIG. 2A

```
         10         30         50
TCACTATAGGGCGAATTGGGTACGGGCCCCCCCTCGAGGTCGACGGTATCGATAAGCTTG
         70         90        110
ATATCGAATTCGGCACGAGCCGGGCTCGGAGAGGTGACGGAACCGGGGCTGGTAGCATAG
        130        150        170
TTTGATTTGATGATGGAGCCAACACAGGGGTTGGAGCTGGTACCGGTGAAGCTGAGGCTA
        190        210        230
AAAAGGTTCCTGGAGTAGACGATGGAGCCATAACTGGAACCGGAGTCTGTGAATGAAGCC
        250        270        290
AGGACAGGAGCAGCACCTGGCGATGGTGCCAGGACCCGGAAGAGGAGCCAGAGGAGGAGCT
        310        330        350
GGAGAAGGAGCCAGAATTGCTGTCTCGTGTGGAGCCGCCCATATAGGAGCCAGGGGTGGCTAGA
        370        390        410
GCCTGAGAATGCAGAAGATGCTGGAGCCAGAAGGGAAGCCTGAGCTGGAGCTGGATTTGG
        430        450        470
TGCTGACGGAAAAGGACTGGCCAGAGCCGAAGCTGCCACCAGGACAGGTGAGCATTCTG
        490        510        530
GGGCCACGGTTGAGTTCAACCCCACTGACTTCAGGTGAAGACTGTGGACCAGCTTGAGAA
        550        570        590
GAGGCCTCACCAGAGTGGGTGTGGGGCATGGGGCTCGAGCAGTACCCAGAGTAGGTGTG
        610        630        650
GGTAGCCCGGCCAGGGGTTAACGTGGGCCAATTGAGGAACAGGAGTCAGTCCATCCCGAGGGGGTT
        670        690        710
TCGGAGGCCCGGGTGCTTGGGCCCAATTGAGGAACAGGAGTCAGTCCATCCCGAGGGGGTT
        730        750        770
GTCTCACTACAATCTTCACACGCCCTTTATTATTCACCATGGTTGGTGCCACCTGGTTAGC
        790        810        830
AGCAAGCGGAAGGCTGAGGCTGAGGGGGTGTTACTGGGGGTCGAAGAAGCCAG
```

MATCH WITH FIG. 2B

FIG. 2B

MATCH WITH FIG. 2A

CACAGAGACAGGGTAGGGCCAGGGTCGGGGCCACGGCCTGGATGAGGCCCACATGGC
850                 870                 890
                                              M  R  P  T  W  A

AGGCTGGCTGATGAGATGGTGCTGCCCCCTGCTGACACGAGGTGCACCACATTCCTTTG
       910                 930                 950
G  W  L  M  R  W  C  C  P  P  A  D  T  R  C  T  F  L  C

CAGCGGGCGGGCTGCCCACAGCAAGCTGGCCACCTGGCGCACCATCCAAATACAGCTT
             970                 990                1010
S  G  R  A  A  P  Q  Q  A  G  A  P  G  H  H  P  K  Y  S  L

GTTTCCCTGGATTTGGAAGGTGAGAGGTTTGCTTCCCCTCCATTAACCACTGACGTTGT
       1030                1050                1070
F  P  W  I  W  K  V  R  G  L  L  P  P  P  L  T  T  D  V  V

GCCAGTGAGACTAACTCTCCGGCCAATCTGTCCGGGCTGACCTCCTTCGCGGGCGTGG
             1090                1110                1130
P  V  R  L  T  L  R  A  N  L  S  A  A  D  L  L  R  G  R  G

CCTACCTCTTCCTCATGTTCCACACTGTCCCCGCACAGCCCGACTTTCACTTGAGGGCTG
       1150                1170                1190
L  P  L  P  H  V  P  H  C  P  R  T  A  R  L  S  L  E  G  W

GTTCCTGCGGCAGGGCTTGCTGGACACAAACCTCACTGCTTCGGTGGCCACACTGCTGGC
             1210                1230                1250
F  L  R  Q  G  L  L  D  T  N  L  T  A  S  V  A  T  L  L  A

CATCGCCGTGGAGCGGCACCGCAGTGTGATGGCCGTGCAGCTGCACAGCCGCCTGCCCG
       1270                1290                1310
I  A  V  E  R  H  R  S  V  M  A  V  Q  L  H  S  R  L  P  R

TGGCCGGCGTGGTCATGCTCATTGTGGGCGTGTGGGTGGCTGCCCTGGGCCTGGGGCTGCT
             1330                1350                1370
G  R  V  V  M  L  I  V  G  V  W  V  A  A  L  G  L  G  L  L
       1390                1410                1430

MATCH WITH FIG. 2C

FIG. 2C

MATCH WITH FIG. 2B

GCCTGCCCACTTCCTGGCACTGCCTCTGTGCCCTGGACCGCTCCTCAGGCATGGCACCCT
P  A  H  S  W  H  C  L  C  A  L  D  R  S  S  R  M  A  P  L
                1450                    1470                    1490

GCTCAGCCGCTCCTATTTGGCCGTGTGGGCTCTGTCTGAGCCTGTCTTCCTGCTCAT
L  S  R  S  Y  L  A  V  W  A  L  S  S  L  L  V  F  L  L  M
                1510                    1530                    1550

GGTGGCTGTGTACACCCGCATTTTCTTCTACGTGCGGGCGAGTGCAGCGCATGGCAGA
V  A  V  Y  T  R  I  F  F  Y  V  R  R  V  Q  R  M  A  E
                1570                    1590                    1610

GCATGTCAGCTGCCACCCCGCTACCGAGAGACCACGCTCAGCCTGGTCAAGACTGTTGT
H  V  S  C  H  P  R  Y  R  E  T  T  L  S  L  V  K  T  V  V
                1630                    1650                    1670

CATCATCCTGGGGGCGTTCGTGGTCTGCTGGACACCAGGCCAGGTGGTACTGCTCCTGGA
I  I  L  G  A  F  V  V  C  W  T  P  G  Q  V  L  L  L  D
                1690                    1710                    1730

TGGTTTAGGCTGTGAGTCCTGCAATGTCCTGGCGTTAGAAAAGTACTTCTTGCTGTTGGC
G  L  G  C  E  S  C  N  V  L  A  L  E  K  Y  F  L  L  A
                1750                    1770                    1790

CGAGCCAACCTCACTGGTCAATGCTGCTGTGTACTCTTGCCGAGATGCTGAGATGCGCCG
E  P  T  S  L  V  N  A  A  V  Y  S  C  R  D  A  E  M  R  R
                1810                    1830                    1850

CACCTTCCGCCGCCTTCTCCTGCTGCGGGTGCCCCCTCCGGTCCACCCGCCGAGTCTGTCC
T  F  R  R  L  L  L  L  R  V  P  P  P  V  H  P  R  V  C  P

Match with FIG. 2D

FIG. 2D

MATCH WITH FIG. 2C

```
          1870                  1890                  1910
ACTATACATCCCTCTGCCCCAGGGAGGTGCCAGCACTCGCATCATGCTTCCCGAGAACGGCC
 L  Y  I  L  C  P  G  R  C  Q  H  S  H  H  A  S  R  E  R  P
          1930                  1950                  1970
ACCCACTGATGGACTCCACCCTTTAGCTACCTTGAACTACAGCGGTACGCGGCAAGCAAC
 P  T  D  G  L  H  P  L  A  T  L  N  Y  S  G  T  R  Q  A  T
          1990                  2010                  2030
AAATCCACAGCCCCTGATGACTTGTGGGTGCTCCTGGCTCAACCTCGTGCCGAAT
 N  P  Q  P  L  M  T  C  G  C  S  W  L  N  P  T  S  C  R  I
          2050                  2070                  2090
TCCTGCAGCCCGGGGATCCACTAGTTCTAGAGCGGCCGCCACCGGGTGGAGCTCCAGCT
 P  A  A  R  G  I  H  *
          2110                  2130                  2150
TTTGTTCCCTTTAGTGAGGGTTAATTTCGAGCTTGGCGTAATCATGGTCATAGCTGTTTC
          2170
CTGTGTGAAATTGTTATCCGCTCAC
```

FIG. 3A

```
CGGCACGAGCATAAGAAGACAGAGAGAACTGAGTATCCTCCCAAAGGTGACACTGGAAGC
                10              30              50
AATGAACACCACAGTAATGCAAGGCTTCAACAGATCTAAGCGGTGCCCCAAAGACACTCG
 M  N  T  T  V  M  Q  G  F  N  R  S  K  R  C  P  K  D  T  R
                70              90             110
GATAGTACAGCTGGTATTCCCAGCCCTCTACACAGTGGTTTTCTTGACCGGAATCCTGCT
  I  V  Q  L  V  F  P  A  L  Y  T  V  V  F  L  T  G  I  L  L
               130             150             170
GAATACTTTGGCTCTGTGGGTGTTTGTTCACATCCCCAGCTCCTCCACCTTCATCATCTA
  N  T  L  A  L  W  V  F  V  H  I  P  S  S  S  T  F  I  I  Y
               190             210             230
CCTCAAAAACACTTTGGTGGCCGACTTGATAATGACACTCATGCTTCCTTTCAAAATCCT
  L  K  N  T  L  V  A  D  L  I  M  T  L  M  L  P  F  K  I  L
               250             270             290
CTCTGACTCACACCTGGCACCCTGGCAGCTCAGAGCTTTGTGTGTCGTTTTCTTCGGT
  S  D  S  H  L  A  P  W  Q  L  R  A  F  V  C  R  F  S  S  V
               310             330             350
GATATTTTATGAGAACATCAGACCTTTGAGAAATATTTTCTAAAAAAAACCTGTTTGGGAAA
  I  F  Y  E  T  M  Y  V  G  I  V  L  L  G  L  I  A  F  D  R
               370             390             410
ATTCCTCAAGATCTTCATCTGGTTCTTTTGGTTCTTCATCTCCCTGCCAAATATGATCTT
  F  L  K  I  R  P  L  R  N  I  F  L  K  K  P  V  W  G  K
               430             450             470
AACGGTCTCAATCTTCAATCTTCATCTGGTTCTTTTGGTTCTTCATCTCCCTGCCAAATATGATCTT
  T  V  S  I  F  W  F  F  W  F  F  I  S  L  P  N  M  I  L
               490             510             530
```

MATCH WITH FIG. 3B

FIG. 3B

MATCH WITH FIG. 3A

```
GAGCAACAAGGAAGCAACACCATCGTCTCTGTGAAAAAGTGTGCTTCCTTAAAGGGCCTCT
 S  N  K  E  A  T  P  S  S  V  K  K  C  A  S  L  K  G  P  L
                    610                      630                      650
GGGGCTGAAATGGCATCAAATGGTAAATAACATATGCCAGTTTATTTTCTGGACTGTTTT
 G  L  K  W  H  Q  M  V  N  N  I  C  Q  F  I  F  W  T  V  F
                    670                      690                      710
TATCCTAATGCTTGTGTGTTTATGTGGTTATTGCAAAAAGTATATGATTCTTATAGAAAG
 I  L  M  L  V  F  Y  V  V  I  A  K  K  Y  M  I  L  I  E  S
                    730                      750                      770
TCCAAAAGTAAGGACAGAAAAAACAAAAGCTGGAAGCAAAGTATTTGTTGTCGTG
 P  K  V  R  T  E  K  T  T  K  S  W  K  A  K  Y  L  L  S  W
                    790                      810                      830
GCTGTCTCTTGTTGTGTTTTGCTCCATTTCATTTCGCCAGAGTTCCATATACTCACAGT
 L  S  S  L  C  V  L  H  F  I  S  P  E  F  H  I  L  T  V
                    850                      870                      890
CAAACCAACAATAAGACTGTAGACTGCAAAATCAACTGTTTATTGCTAAAGAAACA
 K  P  T  I  R  L  T  V  D  C  K  I  N  C  L  L  L  K  K  Q
                    910                      930                      950
ACTCTCTTTTTGGCAGCAACTATGTATGCAAGGGAGAAAGACCACAGCATCAAGCCAA
 L  S  F  W  Q  Q  L  T  F  V  W  I  P  *
                    970                      990                     1010
AAAAAATTCACAGAAAAGCTACCATGTATGCAAGGGAGAAAGACCACAGCATCAAGCCAA
                   1030                     1050                     1070
GAAAATCATAGCAGTCAGACAGACAACATAACCTTAGGCTGACAACTGTACATAGGGTA
```

MATCH WITH FIG. 3C

FIG. 3C

Match with FIG. 3B

```
1090                                        1110                                       1130
ACTTCTATTTATTGATGAGAACTTCCGTAGATAATGTGGAAATCCAATTAACCAAGAAAA
        1150                                       1170                                       1190
AAAGATTGGGGCAAATGCTCTCTTACATTTTATTATCCTGGTGTACAGAAAAGATTATAT
        1210                                       1230                                       1250
AAAATTAAATCCACACATAGATCTATTCATAAGCTGAATGAACCATTACTAAGAGAATGCA
        1270                                       1290                                       1310
ACAGGATACAAATGGCCACTAGAGGTCATTATTCTTTCTTTCTTTTTTTTTTT
        1330                                       1350                                       1370
AATTCAAGAGCATTTCACTTTAACATTTTGGAAAAGACTAAGGAGAAACGTATATCCCT
        1390                                       1410                                       1430
ACAAACCTCCCCCTCCAAACACCTTCTTACATTCTTTTCCACAATTCACATAACACTACTG
        1450                                       1470
CTTTTGTGCCCCCTTAAATGTAGATTTGTTGGCTG
```

FIG. 4A

```
TTTTGGGTATTTCTGAGAAAAAGGAAATATTTATAAACCATCCAAAGATCCAGATAATT
         10                  30                  50
TGCAAATAAATTGGAGGTTATAGAGTTATAATCTGAATCCCAAAGGAGACTGCAGCTGA
         70                  90                 110
TGAAAGTGCTTCCAAACTGAAAATTGGACGTGCCTTTACGATGGTAAGCGTTAACAGTC
        130                 150                 170
                                              M  V  S  V  N  S
CCACTGCTTCTATAATGACTCCTTTAAGTACACTTTGTATGGGTGCATGTTCAGCATGGT
        190                 210                 230
 S  H  C  F  Y  N  D  S  F  K  Y  T  L  Y  G  C  M  F  S  M  V
GTTTGTGCTTGGGTTAATATCCAATTGTGTTGCCATATACATTTCATCTGCGTCCCTCAA
        250                 270                 290
 F  V  L  G  L  I  S  N  C  V  A  I  Y  I  F  I  C  V  L  K
AGTCCGAAATGAAACTACAACTTACATGATTAACTTGGCAATGTCAGACTTGCTTTTTGT
        310                 330                 350
 S  P  K  *  N  Y  N  L  H  D  *  L  G  N  V  R  L  A  F  L
 V  R  N  E  T  T  T  Y  M  I  N  L  A  M  S  D  L  L  F  V
TTTTACTTTACCCTTCAGGATTTTTTACTTCACAACACGGAATTGGCCATTGGAGATTT
        370                 390                 410
 F  T  L  P  F  R  I  F  Y  F  T  T  R  N  W  P  F  G  D  L
ACTTTGTAAGATTTCTGTGATGCTGTTTTATACCAACATGTACGGAAGCATTCTGTTCTT
        430                 450                 470
 L  C  K  I  S  V  M  L  F  Y  T  N  M  Y  G  S  I  L  F  L
AACCTGTATTAGTGTAGATCGATTCTGGCAATTGTCTACCCATTAAGTCAAAGACTCT
        490                 510                 530
 T  C  I  S  V  D  R  F  L  A  I  V  Y  P  F  K  S  K  T  L
```

MATCH WITH FIG. 4B

FIG. 4B

MATCH WITH FIG. 4A

```
      550                570                590
AAGAACCAAAAGAAATGCAAAGATTGTTTGCACTGGCGTGTGGTTAACTGTGATCGGAGG
  R  T  K  R  N  A  K  I  V  C  T  G  V  W  L  T  V  I  G  G
                   610                630                650
AAGTGCACCCGCCGTTTTTGTTCAGTGTCTACCCACTCTCAGGTAACATGCCTCAGAAGC
  S  A  P  A  V  F  V  Q  S  T  H  S  Q  G  N  N  A  S  E  A
      670                690                710
CTGCTTTGAAAATTTTCCAGAAGCCACATGGAAAACATATCTCCAAGGATTGTAATTTT
  C  F  E  N  F  P  E  A  T  W  K  T  Y  L  S  R  I  V  I  F
                   730                750                770
CATCGAAATAGTGGGATTTTTATTCCTCTAATTTTAAATGTAACTTGTTCTAGTATGGT
  I  E  I  V  G  F  F  I  P  L  I  L  N  V  T  C  S  S  M  V
      790                810                830
GCTAAAAACTTTAACCAAACCTGTTACATTAAGTAGAAGCAAAATAAACAAAACTAAGGT
  L  K  T  L  T  K  P  V  T  L  S  R  S  K  I  N  K  T  K  V
                   850                870                890
TTTAAAAATGATTTTTGTACATTTGATCATATTCTGTTTTGTTCCTTACAATAT
  L  K  M  I  F  V  H  L  I  F  C  F  C  F  V  P  Y  N  I
      910                930                950
CAATCTTATTTTATATTCTCTTGTGAGAACACAAACATTGTTAATTGCTCAGTAGTGGC
  N  L  I  L  Y  S  L  V  R  T  Q  T  F  V  N  C  S  V  V  A
```

MATCH WITH FIG. 4C

FIG. 4C

Match with FIG. 4B

```
                970         990        1010
AGCAGTAAGGACAATGTACCCAATCACTCTCTGTATTGCTGTTTCCAACTGTGTTTGA
 A  V  R  T  M  Y  P  I  T  L  C  I  A  V  S  N  C  C  F  D
        1030        1050        1070
CCCTATAGTTTACTACTTTACATCGGACACAATTCAGAATTCAATAAAATGAAAAACTG
 P  I  V  Y  Y  F  T  S  D  T  I  Q  N  S  I  K  M  K  N  W
        1090        1110        1130
GTCTGTCAGGAGAAGTGACTTCAGATTCTGAAGTTCATGGTGCAGAGAATTTTATTCA
 S  V  R  R  S  D  F  R  F  S  E  V  H  G  A  E  N  F  I  Q
        1150        1170        1190
GCATAACCTACAGACCCTTAAAAAGTAAGATATTTGACAATGAATCTGCTGCCTGAAATAA
 H  N  L  Q  T  L  K  K  S  K  I  F  D  N  E  S  A  A  *
        1210        1230        1250
AACCATTAGGACTCACTGGGACAGAACTTCAAGTTCCTTCAACTGTGAAAAGTGTCTTT
        1270        1290
TTGGACAAACTATTTTTCCACCTCCAAAAGAAATTAACACA
```

FIG. 5

```
 64 FFLSHLAVVNIAYACNTVPQMLVNLLHPAKPISFAGCMTLDFLFLSFAHT 113
    ||||||||:|:|||||||||||||||||.|.||||  .||||.||.|| |
  1 FFLSHLAIVDIAYACNTVPQMLVNLLDPVKPISYAGCMTQTFLFLTFAIT  50

114 ECLLLVLMSYDRYVAICHPLRYFIIMTWKVCITLGITSWTCGSLLAMVHV 163
    |||||:|||||||||||||||| ||.:|||  |:.:|.:| || .::|
 51 ECLLLVVMSYDRYVAICHPLRYSAIMSWRVCSTMAVTSWIIGVLLSLIHL 100

164 SLILRLPFCGPREINHFFCEILSVLRLACADTWLNQVVIFEACMFILVGP 213
    |:|.||||||..:|||||||||  .:|||||||  ||::.:..: :||||
101 VLLLPLPFCVSQKVNHFFCEITAILKLACADTHLNETMVLAGAVSVLVGP 150

214 LCLVLVSYSHILGGILRLIQSGEGRRKAFSTCSSHLCVVGLFFGSAIVMYM 263
    ::.::|||.|||..||||||||:|:||||||||||||||||||.|.|||:
151 FSSIVVSYACILGAILKIQSEEGQRKAFSTCSSHLCVVGLFYGTAIVMYV 200

264 APKSRHPEEQQKVLFLILQFLS 285
    .:|:  |.||.|:|.|:   ::.
201 GPRHGSPKEQKKYLLLFHSLFN 222
```

FIG. 6A

```
  1 MRPTWAGWLM.RWCCPPADTRCTFL..CSGRAAPQQAGAPGHHPKYSLF  47
    | ||..:::..:::::.:::::     ::    :     |..  .
  1 MGPTSVPLVKAHRSSVSDYVNYDIIVRHYNYTGKLNISADKENSIKLTSV  50

48 PWIW........KVRGLLPPPLTTDVVPVRLTLRANLSAADLLRGRGLPL  89
    .:|:         .:|.|..  ||.  | ..... || ||| | .::
 51 VFILICCFIILENIFVLLTIWKTKKFHRPMYYFIGNLALSDLLAGVAYTA 100

90 PHVPHCPRTARLSLEGWFLRQGLLDTNLTASVATLLAIAVERHRSVMAVQ 139
    :.:|.|..|  :..:|  |||||:|..|.|.|||||  .|:   ::
101 NLLLSGATTYKLTPAQWFLREGSMFVALSASVFSLLAIAIERYITMLKMK 150

140 LHSRLPRGRVVMLIVGVWVAALGLGLLPAHSWHCLCALDRSSRMAPLLSR 189
    ||  .  |.:::| .:|.|||  |.|:|::|:::|:.|:   ||..:
151 LHNGSNNFRLFLLISACWVISLILGGLPIMGWNCISALSSCSTVLPLYHK 200
```

MATCH WITH FIG. 6B

FIG. 6B

MATCH WITH FIG. 5A

```
190 SYLAVWALSSLLVFLLMVAVYTRIFFYVRRRVQRMA..EHVSCHPRYRET 237
    |::  . |   :::|  :|  :|.|||  .||  .||  .:| .|  . |
201 HYILFCTTVFTLLLLSIVILYCRIYSLVRTRSRRLTFRKNISKASRSSE. 249

238 TLSLVKTVVIILGAFVVCWTPGQVVLLD.GLGCESCNVLALEKYFLLLA  286
    ::.|:|||:|:|:|.|:.|| .||  :  :||||| ..|:|  .|||:||
250 NVALLKTVIVLSVFIACWAPLFILLLDVGCKVKTCDILFRAEYFLVLA   299

287 EPTSLVNAAVYSCRDAEMRRTFRRLLLLRVPPPVHPRVCPLYILCPGRCQ 336
    .|  .|: .|.  : |||||.||  |                 |::..:|.
300 VLNSGTNPIIYTLTNKEMRRAFIR.................IMSCCKCP 331

337 HSHHASRERPPTDGLHPLATLNYSGTR............QATNPQPLMTCGC 376
    ..|.::  .|.         .|::::|  ..          ::.|||::|..:|
332 SGDSAGKFKRPI.....IAGMEFSRSKSDNSSHPQKDEGDNPETIMSSG. 375

377 SWLNPTS 383
    :|..|
376 .NVNSSS 381
```

```
  1 MNTTVMQGFNRSKRCPKDTRIVQLVFPALYTVVFLTGILLNTLALWVFVH  50
    :|.|  |..|  |...|  |.|.::|.||::|||:.||||..::  |:|..
  2 INSTSTQPPDES..CSQNLLITQQIIPVLYCMVFIAGILLNGVSGWIFFY  49

51 IPSSSTFIIYLKNTLVADLIMTLMLPFKILSDSHLAPWQLRAFVCRFSSV 100
    :|||..|||||.::.||||||..:|||||.:||||..||||..||||.|.|
 50 VPSSKSFIIYLKNIVIADFVMSLTFPFKILGDSGLGPWQLNVFVCRVSAV  99

101 IFYETMYVGIVLLGLIAFDRFLKIIRPLRNIFLKKPVWGKTVSIFIWFFW 150
    :||.|||||||||.||||||||.|:||.||:|||:  |.::|  .:||||
100 LFYVNMYVSIVFFGLISFDRYYKIVKPLWTSFIQSVSYSKLLSVIVWMLM 149

151 FFISLPNMILSNKEATPSSVVKKCASLKGPLGLKWHQMVNNICQFIFWTVF 200
    .::.:|||:||.|..   ||.||||  .||..||:|:.|||  |.|||||.|| ||
150 LLAVPNIILTNQSVREVTQIKCIELKSELGRKWHKASNYIFVAIFWIVF 199
201 ILMLVFYVVIAKK.YMILIESPKVRTEKTTKSWKAKYLLSWLSSLCVL.. 247
    :|::|||..|.||.|| :| ||  .||.:|.  :: .|::|.::
200 LLIVFYTAITKKIFKSHLKSSRNSTSVKKKSSRNIFSIVFVFFVCFVPY 249

248 ..........LHFISPEFHILTVKPTIRLTVDC......KINCLLL.  277
    |::..|||...|..:|.  .|...|:::|
250 HIARIPYTKSQTEAHYSCQSKEILRYMKEFTLLLSAANVCLDPIIYFFLC 299

278 ..........KKQLSFWQQ..LTFVWIP 293
    |:::..|||:|::|.
300 QPFREILCKKLHIPLKAQNDLDISRIK  326
```

FIG. 7

6   SSHCFYNDSFKYTLYGCMFSMVFVLGVISNCVAIYIFICVLKVRNETTTYMINLAMSDLL   65
    SS+C    DSFKYTLYGC+FSMVFVLG+I+NCVAIYIF    LKVRNETTTYM+NLA+SDLL
3   SSNCSTEDSFKYTLYGCVFSMVFVLGLIANCVAIYIFTFTLKVRNETTTYMLNLAISDLL   62

66  FVFTLPFRIFYFTTRNWPFGDLLCKISVMLFYTNMYGSILFLTCISVDRFLAIVYPFKSK   125
    FVFTLPFRI+YF    RNWPFGD+LCKISV LFYTNMYGSILFLTCISVDRFLAIV+PF+SK
63  FVFTLPFRIYYFVVRNWPFGDVLCKISVTLFYTNMYGSILFLTCISVDRFLAIVHPFRSK   122

126 TLRTKRNAKIVCTGVWLTVIGGSAPAVFVQSTHSQGNNASEACFENFPEATWKTYLSRIV   185
    TLRTKRNA+IVC    VW+TV+ GS PA F QST+ Q N      CFENFPE+TWKTYLSRIV
123 TLRTKRNARIVCVAVWITVLAGSTPASFFQSTNRQNNTEQRTCFENFPESTWKTYLSRIV   182

186 IFIEIVGFFIPLILNVTCSSMVLKTLTKPVTLSRSKINKTKVLKMIFVHLIIFCFCFVPY   245
    IFIEIVGFFIPLILNVTCS+MVL+TL KP+TLSR+K++K KVLKMIFVHL+IFCFCFVPY
183 IFIEIVGFFIPLILNVTCSTMVLRTLNKPLTLSRNKLSKKKVLKMIFVHLVIFCFCFVPY   242

246 NINLILYSLVRTQTFVNCSVVAAVRTMYPITLCIAVSNCCFDPIVYYFTSDTNSEFNKNE   305
    NI LILYSL+RTQT++NCSVV  AVRTMYP+TLCIAVSNCCFDPIVYYFTSDTNSE +K +
243 NITLILYSLMRTQTWINCSVVTAVRTMYPVTLCIAVSNCCFDPIVYYFTSDTNSELDKKQ   302

POLYNUCLEOTIDES ENCODING HUMAN G-PROTEIN COUPLED RECEPTOR GPRZ

The present application is a continuation-in-part of PCT/US95/04079 filed Mar. 30, 1995.

This invention relates to newly identified polynucleotides, polypeptides encoded by such polynucleotides, the use of such polynucleotides and polypeptides, as well as the production of such polynucleotides and polypeptides. More particularly, the polypeptides of the present invention are human 7-transmembrane receptors. The transmembrane receptors are G-protein coupled receptors sometimes hereinafter referred to individually as GPR1, GPR2, GPR3 and GPR4. The invention also relates to inhibiting the action of such polypeptides.

It is well established that many medically significant biological processes are mediated by proteins participating in signal transduction pathways that involve G-proteins and/or second messengers, e.g., cAMP (Lefkowitz, Nature, 351:353–354 (1991)). Herein these proteins are referred to as proteins participating in pathways with G-proteins or PPG proteins. Some examples of these proteins include the GPC receptors, such as those for adrenergic agents and dopamine (Kobilka, B. K., et al., PNAS, 84:46–50 (1987); Kobilka, B. K., et al., Science, 238:650–656 (1987); Bunzow, J. R., et al., Nature, 336:783–787 (1988)), G-proteins themselves, effector proteins, e.g., phospholipase C, adenyl cyclase, and phosphodiesterase, and actuator proteins, e.g., protein kinase A and protein kinase C (Simon, M. I., et al., Science, 252:802–8 (1991)).

For example, in one form of signal transduction, the effect of hormone binding is activation of an enzyme, adenylate cyclase, inside the cell. Enzyme activation by hormones is dependent on the presence of the nucleotide GTP, and GTP also influences hormone binding. A G-protein connects the hormone receptors to adenylate cyclase. G-protein was shown to exchange GTP for bound GDP when activated by hormone receptors. The GTP-carrying form then binds to an activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane α-helices connected by extracellular or cytoplasmic loops. G-protein coupled receptors include a wide range of biologically active receptors, such as hormone, viral, growth factor and neuroreceptors.

G-protein coupled receptors have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include calcitonin, adrenergic, endothelin, CAMP, adenosine, muscarinic, acetylcholine, serotonin, histamine, thrombin, kinin, follicle stimulating hormone, opsins and rhodopsins, odorant, cytomegalovirus receptors, etc.

Most G-protein coupled receptors have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. TM3 is also implicated in signal transduction.

Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the β-adrenoreceptor, phosphorylation by protein kinase A and/or specific receptor kinases mediates receptor desensitization.

The ligand binding sites of G-protein coupled receptors are believed to comprise a hydrophilic socket formed by several G-protein coupled receptors transmembrane domains, which socket is surrounded by hydrophobic residues of the G-protein coupled receptors. The hydrophilic side of each G-protein coupled receptor transmembrane helix is postulated to face inward and form the polar ligand binding site. TM3 has been implicated in several G-protein coupled receptors as having a ligand binding site, such as including the TM3 aspartate residue. Additionally, TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters (see, Johnson et al., Endoc., Rev., 10:317–331 (1989)). Different G-protein α-subunits preferentially stimulate particular effectors to modulate various biological functions in a cell. Phosphorylation of cytoplasmic residues of G-protein coupled receptors have been identified as an important mechanism for the regulation of G-protein coupling of some G-protein coupled receptors.

G-protein coupled receptors are found in numerous sites within a mammalian host, for example, dopamine is a critical neurotransmitter in the central nervous system and is a G-protein coupled receptor ligand.

In accordance with one aspect of the present invention, there are provided novel polypeptides which have been putatively identified as G-protein coupled receptors and biologically active and diagnostically or therapeutically useful fragments and derivatives thereof. The polypeptides of the present invention are of human origin.

In accordance with another aspect of the present invention, there are provided isolated nucleic acid molecules encoding human G-protein coupled receptors, including mRNAs, DNAs, cDNAs, genomic DNA as well as antisense analogs thereof and biologically active and diagnostically or therapeutically useful fragments thereof.

In accordance with a further aspect of the present invention, there is provided a process for producing such polypeptides by recombinant techniques which comprises culturing recombinant prokaryotic and/or eukaryotic host cells, containing a human G-protein coupled receptor nucleic acid sequence, under conditions promoting expression of said protein and subsequent recovery of said protein.

In accordance with yet a further aspect of the present invention, there are provided antibodies against such polypeptides.

In accordance with another embodiment, there is provided a process for using the receptors to screen for receptor antagonists and/or agonists and/or receptor ligands.

In accordance with still another embodiment of the present invention there is provided a process of using such agonists to stimulate the G-protein coupled receptors for the treatment of conditions related to the under-expression of the G-protein coupled receptors.

In accordance with another aspect of the present invention there is provided a process of using such antagonists for inhibiting the action of the G-protein coupled receptors for treating conditions associated with over-expression of the G-protein coupled receptors.

In accordance with yet another aspect of the present invention there is provided non-naturally occurring synthetic, isolated and/or recombinant G-protein coupled receptor polypeptides which are fragments, consensus fragments and/or sequences having conservative amino acid substitutions, of at least one transmembrane domain of the G-protein coupled receptor, such that G-protein coupled receptor polypeptides of the present invention may bind G-protein coupled receptor ligands, or which may also modulate, quantitatively or qualitatively, G-protein coupled receptor ligand binding.

In accordance with still another aspect of the present invention there are provided synthetic or recombinant G-protein coupled receptor polypeptides, conservative substitution and derivatives thereof, antibodies, anti-idiotype antibodies, compositions and methods that can be useful as potential modulators of G-protein coupled receptor function, by binding to ligands or modulating ligand binding, due to their expected biological properties, which may be used in diagnostic, therapeutic and/or research applications.

It is still another object of the present invention to provide synthetic, isolated or recombinant polypeptides which are designed to inhibit or mimic various G-protein coupled receptors or fragments thereof, as receptor types and subtypes.

In accordance with yet a further aspect of the present invention, there is also provided diagnostic probes comprising nucleic acid molecules of sufficient length to specifically hybridize to the G-protein coupled receptor nucleic acid sequences.

In accordance with yet another object of the present invention, there is provided a diagnostic assay for detecting a disease or susceptibility to a disease related to a mutation in a G-protein coupled receptor nucleic acid sequence.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A to 4C show the cDNA sequences and the corresponding deduced amino acid sequences of the four G-protein coupled receptors of the present invention, respectively. The standard one-letter abbreviation for amino acids are used. Sequencing was performed using a 373 Automated DNA sequencer (Applied Biosystems, Inc.). Sequencing accuracy is predicted to be greater than 97% accurate.

FIG. 5 is an illustration of the amino acid homology between GPR1 (top line) and odorant receptor-like protein (bottom line).

FIGS. 6A and 6B illustrate the amino acid homology between GPR2 (top line) and the human Endothelial Differentiation Gene-1 (EDG-1) (bottom line).

FIG. 7 illustrates the amino acid homology between GPR3 (top line) and a human G-protein coupled receptor open reading frame (ORF) (bottom line).

FIG. 8 illustrates the amino acid homology between GPR4 and the chick orphan G-protein coupled receptor (bottom line).

In accordance with an aspect of the present invention, there are provided isolated nucleic acids (polynucleotides) which encode the mature polypeptides having the deduced amino acid sequences of FIGS. 1–4 (SEQ ID No. 2, 4, 6 and 8) or for the mature polypeptides encoded by the cDNAs of the clones deposited as ATCC Deposit No. 75981 (GPR1), 75976 (GPR2), 75979 (GPR3), 75983 (GPR4) on Dec. 16, 1994.

The ATCC numbers referred to above are directed to a biological deposit with the ATCC, Patent Depository, 10801 University Boulevard, Manassas, Va. 20110-2209. Since the strain referred to is being maintained under the terms of the Budapest Treaty, it will be made available to a patent office signatory to the Budapest Treaty.

A polynucleotide encoding the GPR1 polypeptide of the present invention may be isolated from the human breast. The polynucleotide encoding GPR1 was discovered in a cDNA library derived from human eight-week-old embryo. It is structurally related to the G protein-coupled receptor family. It contains an open reading frame encoding a protein of 296 amino acid residues. The protein exhibits the highest degree of homology to an odorant receptor-like protein with 66% identity and 83% similarity over a 216 amino acid stretch.

A polynucleotide encoding the GPR2 polypeptide of the present invention may be isolated from human liver, heart and leukocytes. The polynucleotide encoding GPR2 was discovered in a cDNA library derived from human adrenal gland tumor. It is structurally related to the G protein-coupled receptor family. It contains an open reading frame encoding a protein of 393 amino acid residues. The protein exhibits the highest degree of homology to human EDG-1 with 30% identity and 52% similarity over a 383 amino acid stretch. Potential ligands to GPR2 include but are not limited to anandamide, serotonin, adrenalin and noradrenalin.

A polynucleotide encoding the GPR3 polypeptide of the present invention may be isolated from human liver, kidney and pancreas. The polynucleotide encoding GPR3 was discovered in a cDNA library derived from human neutrophil. It is structurally related to the G protein-coupled receptor family. It contains an open reading frame encoding a protein of 293 amino acid residues. The protein exhibits the highest degree of homology to a human G-Protein Coupled Receptor open reading frame with 39% identity and 61% similarity over the entire amino acid sequence. Potential ligands to GPR3 include but are not limited to platelet activating factor, thrombin, C5a and bradykinin.

A polynucleotide encoding the GPR4 polypeptide of the present invention may be found in human heart, spleen and leukocytes. The polynucleotide encoding GPR4 was discovered in a cDNA library derived from human twelve-week-old embryo. It is structurally related to the G-protein coupled receptor family. It contains an open reading frame encoding a protein of 344 amino acid residues. The protein exhibits the highest degree of homology to a chick orphan G-protein coupled receptor with 82% identity and 91% similarity over a 291 amino acid stretch. Potential ligands to GPR4 include but are not limited to thrombin, chemokine, and platelet activating factor.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptides may be identical to the coding sequence shown in FIGS. 1–4 (SEQ ID No. 1, 3, 5 and 7) or that of the deposited clones or may be a different coding sequence which coding sequence, as a result of the redundancy or degeneracy of the genetic code, encodes the same mature polypeptides as the DNA of FIGS. 1A to 4C (SEQ ID No. 1, 3, 5 and 7) or the deposited cDNAs.

The polynucleotides which encode the mature polypeptides of FIGS. 1A to 4C (SEQ ID No. 2, 4, 6 and 8) or for the mature polypeptides encoded by the deposited cDNAs may include: only the coding sequence for the mature polypeptide; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode fragments, analogs and derivatives of the polypeptides having the deduced amino acid sequence of FIGS. 1A to 4C (SEQ ID No. 2, 4, 6 and 8) or the polypeptides encoded by the cDNAs of the deposited clones. The variants of the polynucleotides may be a naturally occurring allelic variant of the polynucleotides or a non-naturally occurring variant of the polynucleotides.

Thus, the present invention includes polynucleotides encoding the same mature polypeptides as shown in FIGS. 1–4 (SEQ ID No. 2, 4, 6 and 8) or the same mature polypeptides encoded by the cDNAs of the deposited clones as well as variants of such polynucleotides which variants encode for a fragment, derivative or analog of the polypeptides of FIG. 1A to 4C (SEQ ID No. 2, 4, 6 and 8) or the polypeptides encoded by the cDNAs of the deposited clones. Such nucleotide variants include deletion variants, substitution variants and addition or insertion variants.

As hereinabove indicated, the polynucleotides may have a coding sequence which is a naturally occurring allelic variant of the coding sequences shown in FIGS. 1A to 4C (SEQ ID No. 1, 3, 5 and 7) or of the coding sequences of the deposited clones. As known in the art, an allelic variant is an alternate form of a polynucleotide sequence which may have a substitution, deletion or addition of one or more nucleotides, which does not substantially alter the function of the encoded polypeptides.

The polynucleotides of the present invention may also have the coding sequence fused in frame to a marker sequence which allows for purification of the polypeptides of the present invention. The marker sequence may be a hexahistidine tag supplied by a pQE-9 vector to provide for purification of the mature polypeptides fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1A to 1C, 2A to 2D, 3A to 3C, and 4A to 4C (SEQ ID NO:1, 3, 5 and 7) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, 3, 5 and 7 for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides. The deposit(s) referred to herein will be maintained under the terms of the Budapest Treaty on the International Recognition of the Deposit of Microorganisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to G-protein coupled receptor polypeptides which have the deduced amino acid sequences of FIGS. 1A to 4C (SEQ ID No. 2, 4, 6 and 8) or which have the amino acid sequences encoded by the deposited cDNAs, as well as fragments, analogs and derivatives of such polypeptides.

The terms "fragment," "derivative" and "analog" when referring to the polypeptides of FIGS. 1A to 4C (SEQ ID No. 2, 4, 6 and 8) or that encoded by the deposited cDNAs, means a polypeptide which either retains substantially the same biological function or activity as such polypeptide, i.e. functions as a G-protein coupled receptor, or retains the ability to bind the ligand or the receptor even though the polypeptide does not function as a G-protein coupled receptor, for example, a soluble form of the receptor. An analog includes a proprotein which can be activated by cleavage of the proprotein portion to produce an active mature polypeptide.

The polypeptides of the present invention may be recombinant polypeptides, a natural polypeptides or synthetic polypeptides, preferably recombinant polypeptides.

The fragment, derivative or analog of the polypeptides of FIGS. 1A to 4C (SEQ ID No. 2, 4, 6 and 8) or that encoded by the deposited cDNAs may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide which is employed for purification of the mature polypeptide. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2, 4, 6 and 8 (in particular the mature polypeptide) as well as polypeptides which have at least 70% similarity (preferably at least 70% identity) to the polypeptide of SEQ ID NO:2, 4, 6 and 8 and more preferably at least 90% similarity (more preferably at least 90% identity) to the polypeptide of SEQ ID NO:2, 4, 6 and 8 and still more preferably at least 95% similarity (still more preferably at least 90% identity) to the polypeptide of SEQ ID NO:2, 4, 6 and 8 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention. The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the G-protein coupled receptor genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella typhimurium; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); pTRC99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., U.S.A.). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The G-protein coupled receptor polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

Fragments of the full length G-protein coupled receptor genes may be employed as a hybridization probe for a cDNA library to isolate the full length genes and to isolate other genes which have a high sequence similarity to the gene or similar biological activity. Probes of this type generally have at least 20 bases. Preferably, however, the probes have at least 30 bases and may contain, for example, 50 bases or more. In many cases, the probe has from 20 to 50 bases. The probe may also be used to identify a cDNA clone corresponding to a full length transcript and a genomic clone or clones that contain the complete G-protein coupled receptor gene including regulatory and promotor regions, exons, and introns. As an example of a screen comprises isolating the coding region of the G-protein coupled receptor gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The G-protein coupled receptors of the present invention may be employed in a process for screening for antagonists and/or agonists for the receptor.

In general, such screening procedures involve providing appropriate cells which express the receptor on the surface thereof. Such cells include cells from mammals, yeast, drosophila or *E. Coli*. In particular, a polynucleotide encoding the receptor of the present invention is employed to transfect cells to thereby express the respective G-protein coupled receptor. The expressed receptor is then contacted with a test compound to observe binding, stimulation or inhibition of a functional response.

One such screening procedure involves the use of melanophores which are transfected to express the respective G-protein coupled receptor of the present invention. Such a screening technique is described in PCT WO 92/01810 published Feb. 6, 1992.

Thus, for example, such assay may be employed for screening for a receptor antagonist by contacting the melanophore cells which encode the G-protein coupled receptor with both the receptor ligand and a compound to be screened. Inhibition of the signal generated by the ligand indicates that a compound is a potential antagonist for the receptor, i.e., inhibits activation of the receptor.

The screen may be employed for determining an agonist by contacting such cells with compounds to be screened and determining whether such compound generates a signal, i.e., activates the receptor.

Other screening techniques include the use of cells which express the G-protein coupled receptor (for example, transfected CHO cells) in a system which measures extracellular pH changes caused by receptor activation, for example, as described in Science, volume 246, pages 181–296 (October 1989). For example, potential agonists or antagonists may be contacted with a cell which expresses the G-protein coupled receptor and a second messenger response, e.g. signal transduction or pH changes, may be measured to determine whether the potential agonist or antagonist is effective.

Another such screening technique involves introducing RNA encoding the G-protein coupled receptors into Xenopus oocytes to transiently express the receptor. The receptor oocytes may then be contacted in the case of antagonist screening with the receptor ligand and a compound to be screened, followed by detection of inhibition of a calcium signal.

Another screening technique involves expressing the G-protein coupled receptors in which the receptor is linked to a phospholipase C or D. As representative examples of such cells, there may be mentioned endothelial cells, smooth muscle cells, embryonic kidney cells, etc. The screening for an antagonist or agonist may be accomplished as hereinabove described by detecting activation of the receptor or inhibition of activation of the receptor from the phospholipase second signal.

Another method involves screening for antagonists by determining inhibition of binding of labeled ligand to cells which have the receptor on the surface thereof. Such a method involves transfecting a eukaryotic cell with DNA encoding the G-protein coupled receptor such that the cell expresses the receptor on its surface and contacting the cell with a potential antagonist in the presence of a labeled form of a known ligand. The ligand can be labeled, e.g., by radioactivity. The amount of labeled ligand bound to the receptors is measured, e.g., by measuring radioactivity of the receptors. If the potential antagonist binds to the receptor as determined by a reduction of labeled ligand which binds to the receptors, the binding of labeled ligand to the receptor is inhibited.

G-protein coupled receptors are ubiquitous in the mammalian host and are responsible for many biological functions, including many pathologies. Accordingly, it is desirous to find compounds and drugs which stimulate the G-protein coupled receptors on the one hand and which can antagonize a G-protein coupled receptor on the other hand, when it is desirable to inhibit the G-protein coupled receptor.

For example, agonists for G-protein coupled receptors may be employed for therapeutic purposes, such as the treatment of asthma, Parkinson's disease, acute heart failure, hypotension, urinary retention, and osteoporosis.

In general, antagonists to the G-protein coupled receptors may be employed for a variety of therapeutic purposes, for example, for the treatment of hypertension, angina pectoris, myocardial infarction, ulcers, asthma, allergies, benign prostatic hypertrophy and psychotic and neurological disorders, including schizophrenia, manic excitement, depression, delirium, dementia or severe mental retardation, dyskinesias, such as Huntington's disease or Gilles dila Tourett's syndrome, among others. G-protein coupled receptor antagonists have also been useful in reversing endogenous anorexia and in the control of bulimia.

Examples of G-protein coupled receptor antagonists include an antibody, or in some cases an oligopeptide, which binds to the G-protein coupled receptors but does not elicit a second messenger response such that the activity of the G-protein coupled receptors is prevented. Antibodies include anti-idiotypic antibodies which recognize unique determinants generally associated with the antigen-binding site of an antibody. Potential antagonists also include proteins which are closely related to the ligand of the G-protein coupled receptors, i.e. a fragment of the ligand, which have lost biological function and when binding to the G-protein coupled receptors, elicit no response.

A potential antagonist also includes an antisense construct prepared through the use of antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix -see Lee et al., Nucl. Acids Res., 6:3073 (1979); Cooney et al, Science, 241:456 (1988); and Dervan et al., Science, 251: 1360 (1991)), thereby preventing transcription and the production of G-protein coupled receptors. The antisense RNA oligonucleotide hybridizes to the mRNA in vivo and blocks translation of mRNA molecules into G-protein coupled receptors (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of G-protein coupled receptors.

Another potential antagonist is a small molecule which binds to the G-protein coupled receptor, making it inaccessible to ligands such that normal biological activity is prevented. Examples of small molecules include but are not limited to small peptides or peptide-like molecules.

Potential antagonists also include a soluble form of a G-protein coupled receptor, e.g. a fragment of the receptors, which binds to the ligand and prevents the ligand from interacting with membrane bound G-protein coupled receptors.

This invention additionally provides a method of treating an abnormal condition related to an excess of G-protein coupled receptor activity which comprises administering to a subject the antagonist as hereinabove described along with a pharmaceutically acceptable carrier in an amount effective to block binding of ligands to the G-protein coupled receptors and thereby alleviate the abnormal conditions.

The invention also provides a method of treating abnormal conditions related to an under-expression of G-protein coupled receptor activity which comprises administering to a subject a therapeutically effective amount of the agonist described above in combination with a pharmaceutically acceptable carrier, in an amount effective to enhance binding of ligands to the G-protein coupled receptor and thereby alleviate the abnormal conditions.

The soluble form of the G-protein coupled receptors, antagonists and agonists may be employed in combination with a suitable pharmaceutical carrier. Such compositions comprise a therapeutically effective amount of the antagonist or agonist, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the topical, intravenous, intraperitoneal, intramuscular, subcutaneous, intranasal or intradermal routes. The pharmaceutical compositions are administered in an amount which is effective for treating and/or prophylaxis of the specific indication. In general, the pharmaceutical compositions will be administered in an amount of at least about 10 $\mu$g/kg body weight and in most cases they will be administered in an amount not in excess of about 8 mg/Kg body weight per day. In most cases, the dosage is from about 10 $\mu$g/kg to about 1 mg/kg body weight daily, taking into account the routes of administration, symptoms, etc.

The G-protein coupled receptor polypeptides, and antagonists or agonists which are polypeptides, may be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and $\beta$-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The present invention also provides a method for determining whether a ligand not known to be capable of binding to a G-protein coupled receptor can bind to such receptor which comprises contacting a mammalian cell which expresses a G-protein coupled receptor with the ligand under conditions permitting binding of ligands to the G-protein coupled receptor, detecting the presence of a ligand which binds to the receptor and thereby determining whether the ligand binds to the G-protein coupled receptor.

This invention further provides a method of screening drugs to identify drugs which specifically interact with, and bind to, the human G-protein coupled receptors on the surface of a cell which comprises contacting a mammalian cell comprising an isolated DNA molecule encoding the G-protein coupled receptor with a plurality of drugs, determining those drugs which bind to the mammalian cell, and thereby identifying drugs which specifically interact with and bind to a human G-protein coupled receptor of the present invention.

This invention also provides a method of detecting expression of the G-protein coupled receptor on the surface of a cell by detecting the presence of mRNA coding for a G-protein coupled receptor which comprises obtaining total mRNA from the cell and contacting the mRNA so obtained with a nucleic acid probe comprising a nucleic acid molecule of at least 15 nucleotides capable of specifically hybridizing with a sequence included within the sequence of a nucleic acid molecule encoding a human G-protein coupled receptor under hybridizing conditions, detecting the presence of mRNA hybridized to the probe, and thereby detecting the expression of the G-protein coupled receptor by the cell.

This invention is also related to the use of the G-protein coupled receptor genes as part of a diagnostic assay for detecting diseases or susceptibility to diseases related to the presence of mutations in the G-protein coupled receptor genes. Such diseases, by way of example, are related to cell transformation, such as tumors and cancers.

Individuals carrying mutations in the human G-protein coupled receptor genes may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding the G-protein coupled receptor proteins can be used to identify and analyze G-protein coupled receptor mutations. For example, deletions and insertions can be detected by a change in size of the amplified product in comparison to the normal genotype. Point mutations can be identified by hybridizing amplified DNA to radiolabeled G-protein coupled receptor RNA or alternatively, radiolabeled G-protein coupled receptor antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, U.S.A., 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: A Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies.

The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 μg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1
Bacterial Expression and Purification of GPR1

The DNA sequence encoding GPR1, ATCC # 75981, is initially amplified using PCR oligonucleotide primers corresponding to the 5' and 3' end sequences of the processed G-protein coupled receptor nucleotide sequence. Additional nucleotides corresponding to the GPR1 nucleotide sequence are added to the 5' and 3' sequences respectively. The 5' oligonucleotide primer has the sequence 5' GACTAAAGCTTAATGAGTAGTGAAATGGTG 3' (SEQ ID No. 9) contains a HindIII restriction enzyme site followed by 19 nucleotides of G-protein coupled receptor coding sequence starting from the presumed terminal amino acid of the processed protein. The 3' sequence 5' GAACTTCTAGACCCTCAGGGTTGTAAATCAG 3' (SEQ ID No. 10) contains complementary sequences to an XbaI site and is followed by 20 nucleotides of GPR1 coding sequence. The restriction enzyme sites correspond to the restriction enzyme sites on the bacterial expression vector pQE-9 (Qiagen, Inc. Chatsworth, Calif.). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 is then digested with HindIII and XbaI. The amplified sequences are ligated into pQE-9 and are inserted in frame with the sequence encoding for the histidine tag and the RBS. The ligation mixture is then used to transform E. coli strain M15/rep 4 (Qiagen, Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized G-protein coupled receptor is purified from this solution by chromatography on a Nickel-Chelate column under conditions that allow for tight binding by proteins containing the 6-His tag (Hochuli, E. et al., J. Chromatography 411:177–184 (1984)). GPR1 is eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein is dialyzed to 10 mmolar sodium phosphate.

EXAMPLE 2
Bacterial Expression and Purification of GPR2

The DNA sequence encoding GPR2, ATCC # 75976, is initially amplified using PCR oligonucleotide primers corresponding to the 5' and 3' end sequences of the processed GPR2 coding sequence. Additional nucleotides corresponding to GPR2 coding sequence are added to the 5' and 3' sequences respectively. The 5' oligonucleotide primer has the sequence 5' GACTAAAGCTTAATGAGGCCCACATGGGCA 3' (SEQ ID No. 11) contains a HindIII restriction enzyme site followed by 19 nucleotides of GPR2 coding sequence starting from the presumed terminal amino acid of the processed protein. The 3' sequence 5' GAACTTCTAGACGAACTAGTGGATCCCCCCGG 3' (SEQ ID No. 12) contains complementary sequences to an XbaI site and is followed by 21 nucleotides of GPR2 coding sequence. The restriction enzyme sites correspond to the restriction enzyme sites on the bacterial expression vector pQE-9 (Qiagen, Inc. Chatsworth, Calif.). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 is then digested with HindIII and XbaI. The amplified sequences are ligated into pQE-9 and are inserted in frame with the sequence encoding for the histidine tag and the RBS. The ligation mixture is then used to transform E. coli strain M15/rep 4 (Qiagen, Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized GPR2 is purified from this solution by chromatography on a Nickel-Chelate column under conditions that allow for tight binding by proteins containing the 6-His tag (Hochuli, E. et al., J. Chromatography 411:177–184 (1984)). GPR2 is eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein is dialyzed to 10 mmolar sodium phosphate.

EXAMPLE 3
Bacterial Expression and Purification of GPR3

The DNA sequence encoding GPR3, ATCC # 75979, is initially amplified using PCR oligonucleotide primers corresponding to the 5' and 3' end sequences of the processed G-protein coupled receptor nucleotide sequence. Additional nucleotides corresponding to the GPR3 coding sequence are added to the 5' and 3' sequences respectively. The 5' oligonucleotide primer has the sequence 5' GACTAAAGCTTAATGGCGTCTTTCTCTGCT 3' (SEQ ID No. 13) contains a HindIII restriction enzyme site followed by 19 nucleotides of GPR3 coding sequence starting from the presumed terminal amino acid of the processed protein. The 3' sequence 5' GAACTTCTAGACTTCACACAGTTGTACTAT 3' (SEQ ID No. 14) contains complementary sequences to XbaI site and is followed by 19 nucleotides of GPR3 coding sequence. The restriction enzyme sites correspond to the restriction enzyme sites on the bacterial expression vector pQE-9 (Qiagen, Inc. Chatsworth, Calif.). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 is then digested with XbaI and XbaI. The amplified sequences are ligated into pQE-9 and are inserted in frame with the sequence encoding for the histidine tag and the RBS. The ligation mixture is then used to transform E. coli strain M15/rep 4 (Qiagen Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized GPR3 is purified from this solution by chromatography on a Nickel-Chelate column under conditions that allow for tight binding by proteins containing the 6-His tag (Hochuli, E. et al., J. Chromatography 411:177–184 (1984)). GPR3 is eluted from the column in 6 molar guanidine HCl pH 5.0 and for the purpose of renaturation adjusted to 3 molar guanidine HCl , 100 mM sodium phosphate, 10 mmolar glutathione (reduced) and 2 mmolar glutathione (oxidized). After incubation in this solution for 12 hours the protein is dialyzed to 10 mmolar sodium phosphate.

EXAMPLE 4
Bacterial Expression and Purification of GPR4

The DNA sequence encoding GPR4, ATCC # 75983, is initially amplified using PCR oligonucleotide primers corresponding to the 5' and 3' end sequences of the processed GPR4 nucleotide sequence. Additional nucleotides corresponding to the GPR4 coding sequence are added to the 5' and 3' sequences respectively. The 5' oligonucleotide primer has the sequence 5' GACTAAAGCTTAATGGTAAGCGTTAACAGC 3' (SEQ ID No. 15) contains a HindIII restriction enzyme site followed by 19 nucleotides of GPR4 coding sequence starting from the presumed terminal amino acid of the processed protein. The 3' sequence 5' GAACTTCTAGACTTCAGGCAGCAGATTCATT 3' (SEQ ID No. 16) contains complementary sequences to XbaI site and is followed by 20 nucleotides of GPR4 coding sequence. The restriction enzyme sites correspond to the restriction enzyme sites on the bacterial expression vector pQE-9 (Qiagen, Inc. Chatsworth, Calif.). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 is then digested with HindIII and XbaI. The amplified sequences are ligated into pQE-9 and are inserted in frame with the sequence encoding for the histidine tag and the RBS. The ligation mixture is then used to transform E. coli strain M15/rep 4 (Qiagen, Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized GPR4 is purified from this solution by chromatography on a Nickel-Chelate column under conditions that allow for tight binding by proteins containing the 6-His tag (Hochuli, E. et al., J. Chromatography 411:177–184 (1984)). GPR4 is eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein is dialyzed to 10 mmolar sodium phosphate.

EXAMPLE 5
Expression of Recombinant GPR1 in COS Cells

The expression of plasmid, GPR1 HA is derived from a vector pcDNAI/Amp (Invitrogen) containing: 1) SV40 origin of replication, 2) ampicillin resistance gene, 3) E. coli replication origin, 4) CMV promoter followed by a polylinker region, a SV40 intron and polyadenylation site. A DNA fragment encoding the entire GPR1 precursor and a HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to the target protein allows easy detection of the recombinant protein with an antibody that recognizes the HA epitope.

The plasmid construction strategy is described as follows:

The DNA sequence encoding GPR1, ATCC # 75981, is constructed by PCR using two primers: the 5' primer 5' GTCCAAGCTTGCCACCATGAGTAGTGAAATGGTG 3' (SEQ ID No. 17) contains a HindIII site followed by 18 nucleotides of GPR1 coding sequence starting from the initiation codon; the 3' sequence 5, CTAGCTCGAGTCAAGCGTAGTCTGGGACGTCGTATGGGTAGCAGGGTTGTAAATCAGG 3' (SEQ ID No. 18) contains complementary sequences to an XhoI site, translation stop codon, HA tag and the last 15 nucleotides of the GPR1 coding sequence (not including the stop codon). Therefore, the PCR product contains a HindIII site, GPR1 coding sequence followed by HA tag fused in frame, a translation termination stop codon next to the HA tag, and an XhoI site. The PCR amplified DNA fragment and the vector, pcDNAI/Amp, are digested with HindIII and XhoI restriction enzymes and ligated. The ligation mixture is transformed into *E. coli* strain SURE (Stratagene Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant GPR1, COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the GPR1 HA protein is detected by radiolabeling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media are then collected and cells are lysed with detergent (RIPA buffer (150 mM NaCl, 1% NP-40, 0.1% SDS, 1%-NP-40, 0.5% DOC, 50 mM Tris, pH 7.5). (Wilson, I. et al., Id. 37:767 (1984)). Both cell lysate and culture media are precipitated with a HA specific monoclonal antibody. Proteins precipitated are analyzed on 156 SDS-PAGE gels.

EXAMPLE 6

Expression of Recombinant GPR2 in COS Cells

The expression of plasmid, GPR2 HA is derived from a vector pcDNAI/Amp (Invitrogen) containing: 1) SV40 origin of replication, 2) ampicillin resistance gene, 3) *E. coli* replication origin, 4) CMV promoter followed by a polylinker region, a SV40 intron and polyadenylation site. A DNA fragment encoding the entire GPR2 precursor and a HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The fusion of HA tag to the target protein allows easy detection of the recombinant protein with an antibody that recognizes the HA epitope.

The plasmid construction strategy is described as follows:

The DNA sequence encoding for GPR2, ATCC # 75976, is constructed by PCR using two primers: the 5' primer 5' GTCCAAGCTTGCCACCATGGTTGGTGGCACCTGG 3' (SEQ ID No. 19) contains an HindIII site followed by 18 nucleotides of GPR2 coding sequence starting from the initiation codon; the 3' sequence 5, CTAGCTCGAGTCAAGCGTAGTCTGGGACGTCGTATGGGTAGCAGTGGATCCCCCGTGC 3' (SEQ ID No. 20) contains complementary sequences to an XhoI site, translation stop codon, HA tag and the last 15 nucleotides of the GPR2 coding sequence (not including the stop codon). Therefore, the PCR product contains a HindIII site, GPR2 coding sequence followed by HA tag fused in frame, a translation termination stop codon next to the HA tag, and an XhoI site. The PCR amplified DNA fragment and the vector, pcDNAI/Amp, are digested with HindIII and XhoI restriction enzymes and ligated. The ligation mixture is transformed into *E. coli* strain SURE (Stratagene Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant GPR2, COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the GPR2 HA protein is detecting by radiolabelling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media are then collected and cells are lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). Both cell lysate and culture media are precipitated with a HA specific monoclonal antibody. Proteins precipitated are analyzed on 15% SDS-PAGE gels.

EXAMPLE 7

Expression of Recombinant GPR3 in COS Cells

The expression of plasmid, GPR3 HA is derived from a vector pcDNAI/Amp (Invitrogen) containing: 1) SV40 origin of replication, 2) ampicillin resistance gene, 3) *E. coli* replication origin, 4) CMV promoter followed by a polylinker region, a SV40 intron and polyadenylation site. A DNA fragment encoding the entire GPR3 precursor and a HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The fusion of HA tag to the target protein allows easy detection of the recombinant protein with an antibody that recognizes the HA epitope.

The plasmid construction strategy is described as follows:

The DNA sequence encoding for GPR3, ATCC # 75979, is constructed by PCR using two primers: the 5' primer 5' GTCCAAGCTTGCCACCATGAACACCACAGTAATG 3' (SEQ ID No. 21) contains a HindIII site followed by 18 nucleotides of GPR3 coding sequence starting from the initiation codon; the 3' sequence 5' CTAGCTCGAGTCAAGCGTAGTCTGGGACGTCGTATGGGTAGCAAGGGATCCATACAAATGT 3' (SEQ ID No. 22) contains complementary sequences to an XhoI site, translation stop codon, HA tag and the last 18 nucleotides of the GPR3 coding sequence (not including the stop codon). Therefore, the PCR product contains a HindIII site, GPR3 coding sequence followed by HA tag fused in frame, a translation termination stop codon next to the HA tag, and an XhoI site. The PCR amplified DNA fragment and the vector, pcDNAI/Amp, are digested with HindIII and XhoI restriction enzymes and ligated. The ligation mixture is transformed into *E. coli* strain SURE (Stratagene Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant GPR3, COS cells are transfected with the expression vector by DEAE- DEXTRAN method (J. Sambrook, E. Fritsch, T. Maniatis, Molecular Cloning: A Laboratory Manual, Cold Spring Laboratory Press, (1989)). The expression of the GPR3 HA protein is detected by radiolabelling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media are then collected and cells are lysed with detergent (RIPA buffer (150 mM NaCl, 1% NP-40, 0.10% SDS, 1% NP-40, 0.5% DOC, 50 mM Tris, pH 7.5) (Wilson, I. et al., Id. 37:767 (1984)). Both cell lysate and culture media are precipitated with a HA specific monoclonal antibody. Proteins precipitated are analyzed on 15% SDS-PAGE gels.

EXAMPLE 8
Expression of Recombinant GPR4 in COS Cells

The expression of plasmid, GPR4 HA is derived from a vector pcDNAI/Amp (Invitrogen) containing: 1) SV40 origin of replication, 2) ampicillin resistance gene, 3) *E. coli* replication origin, 4) CMV promoter followed by a polylinker region, a SV40 intron and polyadenylation site. A DNA fragment encoding the entire GPR4 precursor and a HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The fusion of HA tag to the target protein allows easy detection of the recombinant protein with an antibody that recognizes the HA epitope.

The plasmid construction strategy is described as follows:

The DNA sequence encoding for GPR4, ATCC # 75983, is constructed by PCR using two primers: the 5' primer 5' GTCCAAGCTTGCCACCATGGTAAGCGTTAACAGC 3' (SEQ ID No. 23) contains a HindIII site followed by 18 nucleotides of GPR4 coding sequence starting from the initiation codon; the 3' sequence 5' CTAGCTCGAGT-CAAGCGTAGTCTGGGACGTCGTATGGGTAGCAGG CAGCAGATTCATTGTC 3' (SEQ ID No. 24) contains complementary sequences to an XhoI site, translation stop codon, HA tag and the last 18 nucleotides of the GPR4 coding sequence (not including the stop codon). Therefore, the PCR product contains a HindIII site, GPR4 coding sequence followed by HA tag fused in frame, a translation termination stop codon next to the HA tag, and an XhoI site. The PCR amplified DNA fragment and the vector, pcDNAI/ Amp, are digested with Hind III and XhoI restriction enzymes and ligated. The ligation mixture is transformed into *E. coli* strain SURE (Stratagene Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant GPR4, COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the GPR4 HA protein is detected by radiolabelling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media are then collected and cells are lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media are precipitated with a HA specific monoclonal antibody. Proteins precipitated are analyzed on 15% SDS-PAGE gels.

EXAMPLE 9
Cloning and Expression of GPR1 using the Baculovirus Expression System The DNA sequence encoding the full length GPR1 protein, ATCC # 75981, is amplified using PCR oligonucleotide primers corresponding to the 5' and 3' sequences of the gene:

The 5' primer has the sequence 5' CGGGATCCCTCC ATGAG TAGTGAAATGGTG 3' (SEQ ID No. 25) and contains a BamHI restriction enzyme site (in bold) followed by 4 nucleotides resembling an efficient signal for the initiation of translation in eukaryotic cells (Kozak, M., J. Mol. Biol., 196:947–950 (1987) which is just behind the first 18 nucleotides of the GPR1 gene (the initiation codon for translation "ATG" is underlined).

The 3' primer has the sequence 5' CGGGATCCCGCT CAGGGTTGTAAATCAGG 3' (SEQ ID No. 26) and contains the cleavage site for the BamHI restriction endonuclease and 18 nucleotides complementary to the 3' non-translated sequence of the GPR1 gene. The amplified sequences are isolated from a 1% agarose gel using a commercially available kit ("Geneclean," BIO 101 Inc., La Jolla, Calif.). The fragment is then digested with the endonuclease BamHI and then purified again on a 1% agarose gel. This fragment is designated F2.

The vector pRG1 (modification of pVL941 vector, discussed below) is used for the expression of the GPR1 protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonuclease BamHI. The polyadenylation site of the simian virus (SV)40 is used for efficient polyadenylation. For an easy selection of recombinant virus the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid is digested with the restriction enzymes BamHI and then dephosphorylated using calf intestinal phosphatase by procedures known in the art. The DNA is then isolated from a 1 agarose gel using the commercially available kit ("Geneclean" BIO 101 Inc., La Jolla, Calif.). This vector DNA is designated V2.

Fragment F2 and the dephosphorylated plasmid V2 are ligated with T4 DNA ligase. *E. coli* HB101 cells are then transformed and bacteria identified that contained the plasmid (pBacGPR1) with the GPR1 gene using the enzymes BamHI. The sequence of the cloned fragment is confirmed by DNA sequencing.

5 µg of the plasmid pBacGPR1 is cotransfected with 1.0 µg of a commercially available linearized baculovirus ("BaculoGold™ baculovirus DNA", Pharmingen, San Diego, Calif.) using the lipofection method (Felgner et al. Proc. Natl. Acad. Sci. U.S.A., 84:7413–7417 (1987)).

1 µg of BaculoGold™ virus DNA and 5 µg of the plasmid pBacGPR1 are mixed in a sterile well of a microtiter plate containing 50 µl of serum free Grace's medium (Life Technologies Inc., Gaithersburg, Md.). Afterwards 10 µl Lipofectin plus 90 µl Grace's medium are added, mixed and incubated for 15 minutes at room temperature. Then the transfection mixture is added dropwise to the Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the virus are added to the cells, blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculovirus is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-GPR1 at a multiplicity of infection (MOI) of 2. Six hours later the medium is removed and replaced with SF900 II medium minus methionine and cysteine (Life Technologies Inc., Gaithersburg). 42 hours later 5 μCi of $^{35}$S-methionine and 5 μCi 35S cysteine (Amersham) are added. The cells are further incubated for 16 hours before they are harvested by centrifugation and the labelled proteins visualized by SDS-PAGE and autoradiography.

EXAMPLE 10
Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted. The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated polynucleotide comprising a nucleic acid sequence selected from the group consisting of:
   (a) a nucleic acid sequence encoding amino acids 1 to 393 in SEQ ID NO:4;
   (b) a nucleic acid sequence encoding amino acids 2 to 393 in SEQ ID NO:4;
   (c) a nucleic acid sequence encoding the amino acid sequence encoded by the cDNA clone contained in ATCC Deposit No. 75979; and
   (d) a nucleic acid sequence encoding the mature amino acid sequence encoded by the cDNA clone contained in ATCC Deposit No. 75979.

2. The isolated polynucleotide of claim 1, wherein said nucleic acid sequence is (a).

3. The isolated polynucleotide of claim 2, which comprises nucleotides 884 to 2062 in SEQ ID NO:3.

4. The isolated polynucleotide of claim 1, wherein said nucleic acid sequence is (b).

5. The isolated polynucleotide of claim 4, which comprises nucleotides 887 to 2062 in SEQ ID NO:3.

6. The isolated polynucleotide of claim 1, wherein said nucleic acid sequence is (c).

7. The isolated polynucleotide of claim 1, wherein said nucleic acid sequence is (d).

8. The isolated polynucleotide of claim 1, which is DNA.

9. The isolated polynucleotide of claim 1, which is RNA.

10. The isolated polynucleotide of claim 1 further comprising a heterologous polynucleotide.

11. The isolated polynucleotide of claim 10, wherein said heterologous polynucleotide encodes a heterologous polypeptide.

12. A recombinant vector comprising the isolated polynucleotide of claim 1.

13. A genetically engineered host cell comprising the isolated polynucleotide of claim 1 operatively associated with a heterologous regulatory sequence that controls gene expression.

14. A recombinant method of producing a polypeptide that comprises culturing the genetically engineered host cell of claim 13 under conditions such that said polypeptide is expressed, and recovering said polypeptide.

15. A composition comprising the polynucleotide of claim 1.

16. An isolated polynucleotide comprising the complement of a nucleic acid sequence selected from the group consisting of:
   (a) a nucleic acid sequence encoding amino acids 1 to 393 in SEQ ID NO:4;
   (b) a nucleic acid sequence encoding amino acids 2 to 393 in SEQ ID NO:4;
   (c) a nucleic acid sequence encoding the amino acid sequence encoded by the cDNA clone contained in ATCC Deposit No. 75979; and
   (d) a nucleic acid sequence encoding the mature amino acid sequence encoded by the cDNA clone contained in ATCC Deposit No. 75979.

17. An isolated polynucleotide comprising a nucleic acid sequence encoding at least 30 contiguous amino acids of SEQ ID NO:4.

18. The isolated polynucleotide of claim 17, wherein said nucleic acid sequence encodes at least 50 contiguous amino acids of SEQ ID NO:4.

19. An isolated polynucleotide comprising a nucleic acid sequence selected from the group consisting of:
   (a) a nucleic acid sequence encoding the first transmembrane region of SEQ ID NO:4;
   (b) a nucleic acid sequence encoding the second transmembrane region of SEQ ID NO:4;
   (c) a nucleic acid sequence encoding the third transmembrane region of SEQ ID NO:4;
   (d) a nucleic acid sequence encoding the fourth transmembrane region of SEQ ID NO:4;
   (e) a nucleic acid sequence encoding the fifth transmembrane region of SEQ ID NO:4;
   (f) a nucleic acid sequence encoding the sixth transmembrane region of SEQ ID NO:4;
   (g) a nucleic acid sequence encoding the seventh transmembrane region of SEQ ID NO:4; and
   (h) a nucleic acid sequence encoding all seven transmembrane regions of SEQ ID NO:4.

20. The isolated polynucleotide of claim 19, wherein said nucleic acid sequence is (a).

21. The isolated polynucleotide of claim 19, wherein said nucleic acid sequence is (b).

22. The isolated polynucleotide of claim 19, wherein said nucleic acid sequence is (c).

23. The isolated polynucleotide of claim 19, wherein said nucleic acid sequence is (d).

24. The isolated polynucleotide of claim 19, wherein said nucleic acid sequence is (e).

25. The isolated polynucleotide of claim 19, wherein said nucleic acid sequence is (f).

26. The isolated polynucleotide of claim 19, wherein said nucleic acid sequence is (g).

27. The isolated polynucleotide of claim 19, wherein said nucleic acid sequence is (h).

28. The isolated polynucleotide of claim 19 further comprising a heterologous polynucleotide.

29. The isolated polynucleotide of claim 28, wherein said heterologous polynucleotide encodes a heterologous polypeptide.

30. A recombinant vector comprising the isolated polynucleotide of claim 19.

31. A genetically engineered host cell comprising the isolated polynucleotide of claim 19 operatively associated with a heterologous regulatory sequence that controls gene expression.

32. A recombinant method of producing a polypeptide that comprises culturing the genetically engineered host cell of claim 31 under conditions such that said polypeptide is expressed, and recovering said polypeptide.

33. A composition comprising the polynucleotide of claim 19.

34. An isolated polynucleotide comprising the complement of a nucleic acid sequence selected from the group consisting of:
   (a) a nucleic acid sequence encoding the first transmembrane region of SEQ ID NO:4;
   (b) a nucleic acid sequence encoding the second transmembrane region of SEQ ID NO:4;
   (c) a nucleic acid sequence encoding the third transmembrane region of SEQ ID NO:4;
   (d) a nucleic acid sequence encoding the fourth transmembrane region of SEQ ID NO:4;
   (e) a nucleic acid sequence encoding the fifth transmembrane region of SEQ ID NO:4;
   (f) a nucleic acid sequence encoding the sixth transmembrane region of SEQ ID NO:4;
   (g) a nucleic acid sequence encoding the seventh transmembrane region of SEQ ID NO:4; and
   (h) a nucleic acid sequence encoding all seven transmembrane regions of SEQ ID NO:4.

* * * * *

UNITED STATES PATENT AND TRADEMARK OFFICE
CERTIFICATE OF CORRECTION

PATENT NO.   : 5,998,164
DATED        : December 7, 1999
INVENTOR(S)  : Li et al.

Page 1 of 1

It is certified that error appears in the above-identified patent and that said Letters Patent is hereby corrected as shown below:

Title page,
Item [54], Title, please delete "GPRZ" and insert -- GPR2 --.
Item [75], Inventors, please delete "Jian Ni, Gaitherburg, Md."; and please delete "Reiner Gentz, Silver Spring, Md.".

Column 63,
Lines 10, 13, 53 and 55, please delete "75979" and insert -- 75976 --.

Signed and Sealed this

Thirteenth Day of August, 2002

Attest:

JAMES E. ROGAN
Attesting Officer  Director of the United States Patent and Trademark Office

SEQUENCE LISTING (1) GENERAL INFORMATION:

(iii) NUMBER OF SEQUENCES: 30

(2) INFORMATION FOR SEQ ID NO:1:

(i) SEQUENCE CHARACTERISTICS:
      (A) LENGTH: 1713 base pairs
      (B) TYPE: nucleic acid
      (C) STRANDEDNESS: both
      (D) TOPOLOGY: both (ii) MOLECULE TYPE: cDNA (ix) FEATURE:
   (A) NAME/KEY: CDS
   (B) LOCATION: 116..1003

(xi) SEQUENCE DESCRIPTION: SEQ ID NO:1:

```
GGCACGAGGT CATTCAACAT TTATTCAACC AAAAATACTA AGTCAGCTCT ATACAAACTA      60

ATGGAAGGAT ACAGCTATGC AAATATAGAA CACTAAAGTG TTACATGACA GATGT ATG     118
                                                             Met
                                                               1

AGT AGT GAA ATG GTG AAA AAT CAG ACA ATG GTC ACA GAG TTC CTC CTA      166
Ser Ser Glu Met Val Lys Asn Gln Thr Met Val Thr Glu Phe Leu Leu
          5                  10                  15

CTG GGA TTT CTC CTG GGC CCA AGG ATT CAG ATG CTC CTC TTT GGG CTC      214
Leu Gly Phe Leu Leu Gly Pro Arg Ile Gln Met Leu Leu Phe Gly Leu
             20                  25                  30

TTC TCC CTG TTC TAT GTC TTC ACC CTG CTG GGG AAT GGG ACC ATC CTG      262
Phe Ser Leu Phe Tyr Val Phe Thr Leu Leu Gly Asn Gly Thr Ile Leu
 35                  40                  45

GGG CTC ATC TCA CTG GAC TCC AGA CTC CAC ACC CCC ATG TAC TTC TTC      310
Gly Leu Ile Ser Leu Asp Ser Arg Leu His Thr Pro Met Tyr Phe Phe
 50                  55                  60                  65

CTC TCA CAC CTG GCC GTC GTC AAC ATC GCC TAT GCC TGC AAC ACA GTG      358
Leu Ser His Leu Ala Val Val Asn Ile Ala Tyr Ala Cys Asn Thr Val
             70                  75                  80

CCC CAG ATG CTG GTG AAC CTC CTG CAT CCA GCC AAG CCC ATC TCC TTT      406
Pro Gln Met Leu Val Asn Leu Leu His Pro Ala Lys Pro Ile Ser Phe
             85                  90                  95

GCT GGT TGC ATG ACA CTA GAC TTT CTC TTT TTG AGT TTT GCA CAT ACT      454
Ala Gly Cys Met Thr Leu Asp Phe Leu Phe Leu Ser Phe Ala His Thr
            100                 105                 110

GAA TGC CTC CTG TTG GTG CTG ATG TCC TAC GAT CGG TAC GTG GCC ATC      502
Glu Cys Leu Leu Leu Val Leu Met Ser Tyr Asp Arg Tyr Val Ala Ile
115                 120                 125

TGC CAC CCT CTC CGA TAT TTC ATC ATC ATG ACC TGG AAA GTC TGC ATC      550
Cys His Pro Leu Arg Tyr Phe Ile Ile Met Thr Trp Lys Val Cys Ile
130                 135                 140                 145

ACT CTG GGC ATC ACT TCC TGG ACA TGT GGC TCC CTC CTG GCT ATG GTC      598
Thr Leu Gly Ile Thr Ser Trp Thr Cys Gly Ser Leu Leu Ala Met Val
                150                 155                 160

CAT GTG AGC CTC ATC CTA AGA CTG CCC TTT TGT GGG CCT CGT GAA ATC      646
His Val Ser Leu Ile Leu Arg Leu Pro Phe Cys Gly Pro Arg Glu Ile
                165                 170                 175

AAC CAC TTC TTC TGT GAA ATC CTG TCT GTC CTC AGG CTG GCC TGT GCT      694
Asn His Phe Phe Cys Glu Ile Leu Ser Val Leu Arg Leu Ala Cys Ala
                180                 185                 190

GAT ACC TGG CTC AAC CAG GTG GTC ATC TTT GAA GCC TGC ATG TTC ATC      742
Asp Thr Trp Leu Asn Gln Val Val Ile Phe Glu Ala Cys Met Phe Ile
            195                 200                 205

CTG GTG GGA CCA CTC TGC CTG GTG CTG GTC TCC TAC TCA CAC ATC CTG      790
Leu Val Gly Pro Leu Cys Leu Val Leu Val Ser Tyr Ser His Ile Leu
210                 215                 220                 225

GGG GGC ATC CTG AGG ATC CAG TCT GGG GAG GGC CGC AGA AAG GCC TTC      838
Gly Gly Ile Leu Arg Ile Gln Ser Gly Glu Gly Arg Arg Lys Ala Phe
                230                 235                 240

TCC ACC TGC TCC TCC CAC CTC TGC GTA GTG GGA CTC TTC TTT GGS AGC      886
Ser Thr Cys Ser Ser His Leu Cys Val Val Gly Leu Phe Phe Gly Ser
                245                 250                 255

GCC ATC GTC ATG TAC ATG GCC CCT AAG TCC CGC CAT CCT GAG GAG CAG      934
Ala Ile Val Met Tyr Met Ala Pro Lys Ser Arg His Pro Glu Glu Gln
                260                 265                 270
```

```
CAG AAG GTC CTT TTT CTT ATT TTA CAG TTC CTT TCA ACC CCG ATG CTT     982
Gln Lys Val Leu Phe Leu Ile Leu Gln Phe Leu Ser Thr Pro Met Leu
        275                 280                 285

AAA CCC CCT GAT TTA CAA CCC TGA GGAATGTAGA GGGTCAAGGG TGCCCTCCGA   1036
Lys Pro Pro Asp Leu Gln Pro
290                 295

GGAGACCACT GTGCAARGRA AGTCATTCCT AAGGGGTGTG ACATTTGAAC TGCCAGCCCC   1096

AGTTGCCCCG TGGACTCCTG ATGCCCAATT ATTGCCTCAA CCCAGAAAAG TTTACTCCCC   1156

TTTAACTGTG CTTTACTGAC AGAAGGGCAA GCCTTCTCCC GTTTTTTGCA GATAAAATTT   1216

TAGATGTGTT GCAATCATTG GGTTTCTAGG AGATGTGGTT TTATCAGACA ATTTTTTCTT   1276

TTATTTCACA ATTACTTTAA TATCTGTAAA ATAAAGAATT ATTTTAAATC ATTTTCCCAG   1336

TCCCAAAAGT TAAATACAGG CCACTTACTT CTTTAACCAA ATGATATAGT TTGGCTCTGT   1396

GTCCCCACCC AAATCTCATG TCAAATTGTA ATCCCCGCAT GTCAGCGGAG GGACCTGGTG   1456

GGAGGTGATT GGATCATGGG GAGGGATTTC CCCCTTGCTG TTCTGTTGAT AGTGAACGAG   1516

TTCTCACGAA ATCTGATGGT TTAAAAGTGC AGCACTTCTC CCTTTGCTCT CTCTCTCCTG   1576

CTGTGCCATG GTAAGACGTG CCTTGCTTCC CCTGGTGCTT CCGCCATGAT TGTACCTTTC   1636

CTGAGGCCTC TCCAGCCATG TGGAACTGTG AGCCAATTAA ACTTCTTTTC TTTAGAAAAA   1696

AAAAAAAAAA AAAAAA                                                   1713

(2) INFORMATION FOR SEQ ID NO:2:

(i) SEQUENCE CHARACTERISTICS:
        (A) LENGTH: 296 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Ser Glu Met Val Lys Asn Gln Thr Met Val Thr Glu Phe Leu
  1               5                  10                  15

Leu Leu Gly Phe Leu Leu Gly Pro Arg Ile Gln Met Leu Leu Phe Gly
             20                  25                  30

Leu Phe Ser Leu Phe Tyr Val Phe Thr Leu Leu Gly Asn Gly Thr Ile
         35                  40                  45

Leu Gly Leu Ile Ser Leu Asp Ser Arg Leu His Thr Pro Met Tyr Phe
 50                  55                  60

Phe Leu Ser His Leu Ala Val Val Asn Ile Ala Tyr Ala Cys Asn Thr
 65                  70                  75                  80

Val Pro Gln Met Leu Val Asn Leu Leu His Pro Ala Lys Pro Ile Ser
                 85                  90                  95

Phe Ala Gly Cys Met Thr Leu Asp Phe Leu Phe Leu Ser Phe Ala His
            100                 105                 110

Thr Glu Cys Leu Leu Leu Val Leu Met Ser Tyr Asp Arg Tyr Val Ala
        115                 120                 125

Ile Cys His Pro Leu Arg Tyr Phe Ile Ile Met Thr Trp Lys Val Cys
    130                 135                 140

Ile Thr Leu Gly Ile Thr Ser Trp Thr Cys Gly Ser Leu Leu Ala Met
145                 150                 155                 160

Val His Val Ser Leu Ile Leu Arg Leu Pro Phe Cys Gly Pro Arg Glu
                165                 170                 175

Ile Asn His Phe Phe Cys Glu Ile Leu Ser Val Leu Arg Leu Ala Cys
            180                 185                 190
```

```
Ala Asp Thr Trp Leu Asn Gln Val Val Ile Phe Glu Ala Cys Met Phe
    195                 200                 205

Ile Leu Val Gly Pro Leu Cys Leu Val Leu Val Ser Tyr Ser His Ile
210                 215                 220

Leu Gly Gly Ile Leu Arg Ile Gln Ser Gly Glu Gly Arg Arg Lys Ala
225                 230                 235                 240

Phe Ser Thr Cys Ser Ser His Leu Cys Val Val Gly Leu Phe Phe Gly
                245                 250                 255

Ser Ala Ile Val Met Tyr Met Ala Pro Lys Ser Arg His Pro Glu Glu
            260                 265                 270

Gln Gln Lys Val Leu Phe Leu Ile Leu Gln Phe Leu Ser Thr Pro Met
        275                 280                 285

Leu Lys Pro Pro Asp Leu Gln Pro
    290                 295
```

(2) INFORMATION FOR SEQ ID NO:3:

(i) SEQUENCE CHARACTERISTICS:
        (A) LENGTH: 2185 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 884..2062

(xi) SEQUENCE DESCRIPTION: SEQ ID NO:3:

```
TCACTATAGG GCGAATTGGG TACGGGCCCC CCCTCGAGGT CGACGGTATC GATAAGCTTG      60

ATATCGAATT CGGCACGAGC CGGGCTCGGA GAGGTGACGG AACCGGGGCT GGTAGCATAG     120

TTTGATTTGA TGATGGAGCC AACACAGGGG TTGGAGCTGG TACCGGTGAA GCTGAGGCTA     180

AAAAGGTTCC TGGAGTAGAC GATGGAGCCA TAACTGGAAC CGGAGTCTGT GAATGAAGCC     240

AGGACAGGAG CAGCACCTGG CGATGGTGCC AGGACCGGAA GAGGAGCCAG AGGAGGAGCT     300

GGAGAAGGAG CCAGAATTGC TGTCTGTGGA GCCGCCATAG GAGCCAGAGG GGTGGCTAGA     360

GCCTGAGAAT GCAGAAGATG CTGGAGCCAG AAGGGAAGCC TGAGCTGGAG CTGGATTTGG     420

TGCTGACGGA AAAGGACTGG CCAGAGCCGA AGCTGGCACC AGGGACAGGT GAGCATTCTG     480

GGGCCACGGT TGAGTTCAAC CCACTGACTT CAGGTGAAGG ACTGTGGACC AGCTTGAGAA     540

GAGGCCTCAC CAGAGTGGGT GTGGGGCATG GGGGCTCGAG CAGTACCCAG AGTAGGTGTG     600

GGTAGCCCGG CCAGGGGTTA ACGTGGGGCG TGGATTCAAC ACAGCTTGGA AGCCCAGAGC     660

TCGGAGGCCC GGGTGCTTGG GCCAATTGAG GAACAGGAGT CAGTCCATCC CGAGGGGGTT     720

GTCTCACTAC AATCTTCACA CGCCTTTATT ATTCACCATG GTTGGTGGCA CCTGGTTAGC     780

AGCAAGCGGA AGGCTGAGGC CAGTAGGGGC AGGGGTGTTA CTGGGGGTCG AAGAAGCCAG     840

CACAGAGACA GGGTAGGGC CAGGGGTCGG GGCCACGGCC TGG ATG AGG CCC ACA        895
                                            Met Arg Pro Thr
                                             1

TGG GCA GGC TGG CTG ATG AGA TGG TGC TGC CCC CCT GCT GAC ACG AGG       943
Trp Ala Gly Trp Leu Met Arg Trp Cys Cys Pro Pro Ala Asp Thr Arg
  5                  10                  15                  20

TGC ACC ACA TTC CTT TGC AGC GGG CGG GCT GCC CCA CAG CAA GCT GGC       991
Cys Thr Thr Phe Leu Cys Ser Gly Arg Ala Ala Pro Gln Gln Ala Gly
                 25                  30                  35

GCA CCT GGG CAC CAT CCA AAA TAC AGC TTG TTT CCC TGG ATT TGG AAG      1039
Ala Pro Gly His His Pro Lys Tyr Ser Leu Phe Pro Trp Ile Trp Lys
```

```
                      40                    45                    50
GTG AGA GGT TTG CTT CCC CCT CCA TTA ACC ACT GAC GTT GTG CCA GTG         1087
Val Arg Gly Leu Leu Pro Pro Pro Leu Thr Thr Asp Val Val Pro Val
         55                    60                    65

AGA CTA ACT CTC CGC GCC AAT CTG TCC GCG GCT GAC CTC CTT CGC GGG         1135
Arg Leu Thr Leu Arg Ala Asn Leu Ser Ala Ala Asp Leu Leu Arg Gly
     70                    75                    80

CGT GGC CTA CCT CTT CCT CAT GTT CCA CAC TGT CCC CGC ACA GCC CGA         1183
Arg Gly Leu Pro Leu Pro His Val Pro His Cys Pro Arg Thr Ala Arg
 85                    90                    95                   100

CTT TCA CTT GAG GGC TGG TTC CTG CGG CAG GGT TTG CTG GAC ACA AAC         1231
Leu Ser Leu Glu Gly Trp Phe Leu Arg Gln Gly Leu Leu Asp Thr Asn
                 105                   110                   115

CTC ACT GCG TCG GTG GCC ACA CTG CTG GCC ATC GCC GTG GAG CGG CAC         1279
Leu Thr Ala Ser Val Ala Thr Leu Leu Ala Ile Ala Val Glu Arg His
             120                   125                   130

CGC AGT GTG ATG GCC GTG CAG CTG CAC AGC CGC CTG CCC CGT GGC CGC         1327
Arg Ser Val Met Ala Val Gln Leu His Ser Arg Leu Pro Arg Gly Arg
         135                   140                   145

GTG GTC ATG CTC ATT GTG GGC GTG TGG GTG GCT GCC CTG GGC CTG GGG         1375
Val Val Met Leu Ile Val Gly Val Trp Val Ala Ala Leu Gly Leu Gly
     150                   155                   160

CTG CTG CCT GCC CAC TCC TGG CAC TGC CTC TGT GCC CTG GAC CGC TCC         1423
Leu Leu Pro Ala His Ser Trp His Cys Leu Cys Ala Leu Asp Arg Ser
165                   170                   175                   180

TCA CGC ATG GCA CCC CTG CTC AGC CGC TCC TAT TTG GCC GTC TGG GCT         1471
Ser Arg Met Ala Pro Leu Leu Ser Arg Ser Tyr Leu Ala Val Trp Ala
                 185                   190                   195

CTG TCG AGC CTG CTT GTC TTC CTG CTC ATG GTG GCT GTG TAC ACC CGC         1519
Leu Ser Ser Leu Leu Val Phe Leu Leu Met Val Ala Val Tyr Thr Arg
             200                   205                   210

ATT TTC TTC TAC GTG CGG CGG CGA GTG CAG CGC ATG GCA GAG CAT GTC         1567
Ile Phe Phe Tyr Val Arg Arg Arg Val Gln Arg Met Ala Glu His Val
         215                   220                   225

AGC TGC CAC CCC CGC TAC CGA GAG ACC ACG CTC AGC CTG GTC AAG ACT         1615
Ser Cys His Pro Arg Tyr Arg Glu Thr Thr Leu Ser Leu Val Lys Thr
     230                   235                   240

GTT GTC ATC ATC CTG GGG GCG TTC GTG GTC TGC TGG ACA CCA GGC CAG         1663
Val Val Ile Ile Leu Gly Ala Phe Val Val Cys Trp Thr Pro Gly Gln
245                   250                   255                   260

GTG GTA CTG CTC CTG GAT GGT TTA GGC TGT GAG TCC TGC AAT GTC CTG         1711
Val Val Leu Leu Leu Asp Gly Leu Gly Cys Glu Ser Cys Asn Val Leu
                 265                   270                   275

GCG TTA GAA AAG TAC TTC CTA CTG TTG GCC GAG CCA ACC TCA CTG GTC         1759
Ala Leu Glu Lys Tyr Phe Leu Leu Leu Ala Glu Pro Thr Ser Leu Val
             280                   285                   290

AAT GCT GCT GTG TAC TCT TGC CGA GAT GCT GAG ATG CGC CGC ACC TTC         1807
Asn Ala Ala Val Tyr Ser Cys Arg Asp Ala Glu Met Arg Arg Thr Phe
         295                   300                   305

CGC CGC CTT CTC CTG CTG CGC GTG CCT CCG CCA GTC CAC CCG CGA GTC         1855
Arg Arg Leu Leu Leu Leu Arg Val Pro Pro Pro Val His Pro Arg Val
     310                   315                   320

TGT CCA CTA TAC ATC CTC TGC CCA GGG AGG TGC CAG CAC TCG CAT CAT         1903
Cys Pro Leu Tyr Ile Leu Cys Pro Gly Arg Cys Gln His Ser His His
325                   330                   335                   340

GCT TCC CGA GAA CGG CCA CCC ACT GAT GGA CTC CAC CCT TTA GCT ACC         1951
Ala Ser Arg Glu Arg Pro Pro Thr Asp Gly Leu His Pro Leu Ala Thr
                 345                   350                   355

TTG AAC TAC AGC GGT ACG CGG CAA GCA ACA AAT CCA CAG CCC CTG ATG         1999
Leu Asn Tyr Ser Gly Thr Arg Gln Ala Thr Asn Pro Gln Pro Leu Met
```

|     |     |     |     | 360 |     |     |     |     | 365 |     |     |     |     | 370 |     |     |      |
| --- | --- | --- | --- | --- | --- | --- | --- | --- | --- | --- | --- | --- | --- | --- | --- | --- | ---- |
| ACT | TGT | GGG | TGC | TCC | TGG | CTC | AAC | CCA | ACC | TCG | TGC | CGA | ATT | CCT | GCA |     | 2047 |
| Thr | Cys | Gly | Cys | Ser | Trp | Leu | Asn | Pro | Thr | Ser | Cys | Arg | Ile | Pro | Ala |     |      |
|     |     | 375 |     |     |     |     | 380 |     |     |     |     | 385 |     |     |     |     |      |

```
GCC CGG GGG ATC CAC TAG TTCTAGAGCG GCGCCACCGC GGTGGAGCTC                   2095
Ala Arg Gly Ile His
        390

CAGCTTTTGT TCCCTTTAGT GAGGGTTAAT TTCGAGCTTG GCGTAATCAT GGTCATAGCT          2155

GTTTCCTGTG TGAAATTGTT ATCCGCTCAC                                           2185

(2) INFORMATION FOR SEQ ID NO:4:

(i) SEQUENCE CHARACTERISTICS:
        (A) LENGTH: 393 amino acids
        (B) TYPE: amino acid
        (D) TOPOLOGY: linear (ii) MOLECULE TYPE: protein (xi) SEQUENCE DESCRIPTION: SEQ ID NO:4:

Met Arg Pro Thr Trp Ala Gly Trp Leu Met Arg Trp Cys Cys Pro Pro
 1               5                  10                  15

Ala Asp Thr Arg Cys Thr Thr Phe Leu Cys Ser Gly Arg Ala Ala Pro
                20                  25                  30

Gln Gln Ala Gly Ala Pro Gly His His Pro Lys Tyr Ser Leu Phe Pro
        35                  40                  45

Trp Ile Trp Lys Val Arg Gly Leu Leu Pro Pro Leu Thr Thr Asp
 50                  55                  60

Val Val Pro Val Arg Leu Thr Leu Arg Ala Asn Leu Ser Ala Ala Asp
65                  70                  75                  80

Leu Leu Arg Gly Arg Gly Leu Pro Leu Pro His Val Pro His Cys Pro
                85                  90                  95

Arg Thr Ala Arg Leu Ser Leu Glu Gly Trp Phe Leu Arg Gln Gly Leu
            100                 105                 110

Leu Asp Thr Asn Leu Thr Ala Ser Val Ala Thr Leu Leu Ala Ile Ala
            115                 120                 125

Val Glu Arg His Arg Ser Val Met Ala Val Gln Leu His Ser Arg Leu
130                 135                 140

Pro Arg Gly Arg Val Val Met Leu Ile Val Gly Val Trp Val Ala Ala
145                 150                 155                 160

Leu Gly Leu Gly Leu Leu Pro Ala His Ser Trp His Cys Leu Cys Ala
                165                 170                 175

Leu Asp Arg Ser Ser Arg Met Ala Pro Leu Leu Ser Arg Ser Tyr Leu
            180                 185                 190

Ala Val Trp Ala Leu Ser Ser Leu Leu Val Phe Leu Leu Met Val Ala
            195                 200                 205

Val Tyr Thr Arg Ile Phe Phe Tyr Val Arg Arg Val Gln Arg Met
210                 215                 220

Ala Glu His Val Ser Cys His Pro Arg Tyr Arg Glu Thr Thr Leu Ser
225                 230                 235                 240

Leu Val Lys Thr Val Ile Ile Leu Gly Ala Phe Val Val Cys Trp
                245                 250                 255

Thr Pro Gly Gln Val Val Leu Leu Leu Asp Gly Leu Gly Cys Glu Ser
            260                 265                 270

Cys Asn Val Leu Ala Leu Glu Lys Tyr Phe Leu Leu Leu Ala Glu Pro
            275                 280                 285
```

```
Thr Ser Leu Val Asn Ala Ala Val Tyr Ser Cys Arg Asp Ala Glu Met
    290                 295                 300

Arg Arg Thr Phe Arg Arg Leu Leu Leu Leu Arg Val Pro Pro Pro Val
305                 310                 315                 320

His Pro Arg Val Cys Pro Leu Tyr Ile Leu Cys Pro Gly Arg Cys Gln
                325                 330                 335

His Ser His His Ala Ser Arg Glu Arg Pro Pro Thr Asp Gly Leu His
            340                 345                 350

Pro Leu Ala Thr Leu Asn Tyr Ser Gly Thr Arg Gln Ala Thr Asn Pro
        355                 360                 365

Gln Pro Leu Met Thr Cys Gly Cys Ser Trp Leu Asn Pro Thr Ser Cys
    370                 375                 380

Arg Ile Pro Ala Ala Arg Gly Ile His
385                 390
```

(2) INFORMATION FOR SEQ ID NO:5:

(i) SEQUENCE CHARACTERISTICS:
        (A) LENGTH: 1474 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 62..940

(xi) SEQUENCE DESCRIPTION: SEQ ID NO:5:

```
CGGCACGAGC ATAAGAAGAC AGAGAGAACT GAGTATCCTC CCAAAGGTGA CACTGGAAGC        60

A ATG AAC ACC ACA GTA ATG CAA GGC TTC AAC AGA TCT AAG CGG TGC          106
  Met Asn Thr Thr Val Met Gln Gly Phe Asn Arg Ser Lys Arg Cys
  1               5                   10                  15

CCC AAA GAC ACT CGG ATA GTA CAG CTG GTA TTC CCA GCC CTC TAC ACA        154
Pro Lys Asp Thr Arg Ile Val Gln Leu Val Phe Pro Ala Leu Tyr Thr
                20                  25                  30

GTG GTT TTC TTG ACC GGA ATC CTG CTG AAT ACT TTG GCT CTG TGG GTG        202
Val Val Phe Leu Thr Gly Ile Leu Leu Asn Thr Leu Ala Leu Trp Val
            35                  40                  45

TTT GTT CAC ATC CCC AGC TCC TCC ACC TTC ATC ATC TAC CTC AAA AAC        250
Phe Val His Ile Pro Ser Ser Ser Thr Phe Ile Ile Tyr Leu Lys Asn
        50                  55                  60

ACT TTG GTG GCC GAC TTG ATA ATG ACA CTC ATG CTT CCT TTC AAA ATC        298
Thr Leu Val Ala Asp Leu Ile Met Thr Leu Met Leu Pro Phe Lys Ile
    65                  70                  75

CTC TCT GAC TCA CAC CTG GCA CCC TGG CAG CTC AGA GCT TTT GTG TGT        346
Leu Ser Asp Ser His Leu Ala Pro Trp Gln Leu Arg Ala Phe Val Cys
80                  85                  90                  95

CGT TTT TCT TCG GTG ATA TTT TAT GAG ACC ATG TAT GTG GGC ATC GTG        394
Arg Phe Ser Ser Val Ile Phe Tyr Glu Thr Met Tyr Val Gly Ile Val
                100                 105                 110

CTG TTA GGG CTC ATA GCC TTT GAC AGA TTC CTC AAG ATC ATC AGA CCT        442
Leu Leu Gly Leu Ile Ala Phe Asp Arg Phe Leu Lys Ile Ile Arg Pro
            115                 120                 125

TTG AGA AAT ATT TTT CTA AAA AAA CCT GTT TGG GGA AAA ACG GTC TCA        490
Leu Arg Asn Ile Phe Leu Lys Lys Pro Val Trp Gly Lys Thr Val Ser
        130                 135                 140

ATC TTC ATC TGG TTC TTT TGG TTC TTC ATC TCC CTG CCA AAT ATG ATC        538
Ile Phe Ile Trp Phe Phe Trp Phe Phe Ile Ser Leu Pro Asn Met Ile
    145                 150                 155
```

```
TTG AGC AAC AAG GAA GCA ACA CCA TCG TCT GTG AAA AAG TGT GCT TCC    586
Leu Ser Asn Lys Glu Ala Thr Pro Ser Ser Val Lys Lys Cys Ala Ser
160                 165                 170                 175

TTA AAG GGG CCT CTG GGG CTG AAA TGG CAT CAA ATG GTA AAT AAC ATA    634
Leu Lys Gly Pro Leu Gly Leu Lys Trp His Gln Met Val Asn Asn Ile
            180                 185                 190

TGC CAG TTT ATT TTC TGG ACT GTT TTT ATC CTA ATG CTT GTG TTT TAT    682
Cys Gln Phe Ile Phe Trp Thr Val Phe Ile Leu Met Leu Val Phe Tyr
        195                 200                 205

GTG GTT ATT GCA AAA AAG TAT ATG ATT CTT ATA GAA AGT CCA AAA GTA    730
Val Val Ile Ala Lys Lys Tyr Met Ile Leu Ile Glu Ser Pro Lys Val
    210                 215                 220

AGG ACA GAA AAA ACA ACA AAA AGC TGG AAG GCA AAG TAT TTG TTG TCG    778
Arg Thr Glu Lys Thr Thr Lys Ser Trp Lys Ala Lys Tyr Leu Leu Ser
225                 230                 235

TGG CTG TCT TCT TTG TGT GTT TTG CTC CAT TTC ATT TCG CCA GAG TTC    826
Trp Leu Ser Ser Leu Cys Val Leu Leu His Phe Ile Ser Pro Glu Phe
240                 245                 250                 255

CAT ATA CTC ACA GTC AAA CCA ACA ATA AGA CTG ACT GTA GAC TGC AAA    874
His Ile Leu Thr Val Lys Pro Thr Ile Arg Leu Thr Val Asp Cys Lys
                260                 265                 270

ATC AAC TGT TTA TTG CTA AAG AAA CAA CTC TCT TTT TGG CAG CAA CTA    922
Ile Asn Cys Leu Leu Leu Lys Lys Gln Leu Ser Phe Trp Gln Gln Leu
            275                 280                 285

ACA TTT GTA TGG ATC CCT TAA TATACATATT CTTATGTAAA AAATTCACAG       973
Thr Phe Val Trp Ile Pro
            290

AAAAGCTACC ATGTATGCAA GGGAGAAAGA CCACAGCATC AAGCCAAGAA AATCATAGCA  1033

GTCAGACAGA CAACATAACC TTAGGCTGAC AACTGTACAT AGGGGTAACT TCTATTTATT  1093

GATGAGACTT CCGTAGATAA TGTGGAAATC CAATTTAACC AAGAAAAAAA GATTGGGGCA  1153

AATGCTCTCT TACATTTTAT TATCCTGGTG TACAGAAAAG ATTATATAAA ATTTAAATCC  1213

ACATAGATCT ATTCATAAGC TGAATGAACC ATTACTAAGA GAATGCAACA GGATACAAAT  1273

GGCCACTAGA GGTCATTATT TCTTTCTTTC TTTCTTTTTT TTTTTTAAT TTCAAGAGCA   1333

TTTCACTTTA ACATTTTGGA AAAGACTAAG GAGAAACGTA TATCCCTACA AACCTCCCCT  1393

CCAAACACCT TCTTACATTC TTTTCCACAA TTCACATAAC ACTACTGCTT TTGTGCCCCT  1453

TAAATGTAGA TTTGTTGGCT G                                           1474

(2) INFORMATION FOR SEQ ID NO:6:

(i) SEQUENCE CHARACTERISTICS:
        (A) LENGTH: 293 amino acids
        (B) TYPE: amino acid
        (D) TOPOLOGY: linear (ii) MOLECULE TYPE: protein (xi) SEQUENCE DESCRIPTION: SEQ ID NO:6:

Met Asn Thr Thr Val Met Gln Gly Phe Asn Arg Ser Lys Arg Cys Pro
1               5                   10                  15

Lys Asp Thr Arg Ile Val Gln Leu Val Phe Pro Ala Leu Tyr Thr Val
            20                  25                  30

Val Phe Leu Thr Gly Ile Leu Leu Asn Thr Leu Ala Leu Trp Val Phe
        35                  40                  45

Val His Ile Pro Ser Ser Ser Thr Phe Ile Ile Tyr Leu Lys Asn Thr
    50                  55                  60

Leu Val Ala Asp Leu Ile Met Thr Leu Met Leu Pro Phe Lys Ile Leu
65                  70                  75                  80
```

```
Ser Asp Ser His Leu Ala Pro Trp Gln Leu Arg Ala Phe Val Cys Arg
            85                  90                  95

Phe Ser Ser Val Ile Phe Tyr Glu Thr Met Tyr Val Gly Ile Val Leu
        100                 105                 110

Leu Gly Leu Ile Ala Phe Asp Arg Phe Leu Lys Ile Ile Arg Pro Leu
    115                 120                 125

Arg Asn Ile Phe Leu Lys Lys Pro Val Trp Gly Lys Thr Val Ser Ile
    130                 135                 140

Phe Ile Trp Phe Phe Trp Phe Phe Ile Ser Leu Pro Asn Met Ile Leu
145                 150                 155                 160

Ser Asn Lys Glu Ala Thr Pro Ser Ser Val Lys Lys Cys Ala Ser Leu
                165                 170                 175

Lys Gly Pro Leu Gly Leu Lys Trp His Gln Met Val Asn Asn Ile Cys
            180                 185                 190

Gln Phe Ile Phe Trp Thr Val Phe Ile Leu Met Leu Val Phe Tyr Val
        195                 200                 205

Val Ile Ala Lys Lys Tyr Met Ile Leu Ile Glu Ser Pro Lys Val Arg
    210                 215                 220

Thr Glu Lys Thr Thr Lys Ser Trp Lys Ala Lys Tyr Leu Leu Ser Trp
225                 230                 235                 240

Leu Ser Ser Leu Cys Val Leu Leu His Phe Ile Ser Pro Glu Phe His
                245                 250                 255

Ile Leu Thr Val Lys Pro Thr Ile Arg Leu Thr Val Asp Cys Lys Ile
            260                 265                 270

Asn Cys Leu Leu Leu Lys Lys Gln Leu Ser Phe Trp Gln Gln Leu Thr
        275                 280                 285

Phe Val Trp Ile Pro
    290

(2) INFORMATION FOR SEQ ID NO:7:

(i) SEQUENCE CHARACTERISTICS:
        (A) LENGTH: 1301 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 161..1192

(xi) SEQUENCE DESCRIPTION: SEQ ID NO:7:

TTTTGGGTAT TTCTGAGAAA AAGGAAATAT TTATAAAACC ATCCAAAGAT CCAGATAATT      60

TGCAAATAAA TTGGAGGTTA TAGAGGTTAT AATCTGAATC CCAAAGGAGA CTGCAGCTGA     120

TGAAAGTGCT TCCAAACTGA AAATTGGACG TGCCTTTACG ATG GTA AGC GTT AAC      175
                                             Met Val Ser Val Asn
                                              1               5

AGC TCC CAC TGC TTC TAT AAT GAC TCC TTT AAG TAC ACT TTG TAT GGG      223
Ser Ser His Cys Phe Tyr Asn Asp Ser Phe Lys Tyr Thr Leu Tyr Gly
            10                  15                  20

TGC ATG TTC AGC ATG GTG TTT GTG CTT GGG TTA ATA TCC AAT TGT GTT      271
Cys Met Phe Ser Met Val Phe Val Leu Gly Leu Ile Ser Asn Cys Val
        25                  30                  35

GCC ATA TAC ATT TTC ATC TGC GTC CTC AAA GTC CGA AAT GAA ACT ACA      319
Ala Ile Tyr Ile Phe Ile Cys Val Leu Lys Val Arg Asn Glu Thr Thr
    40                  45                  50
```

-continued

| | | | | | | | | | | | | | | | | |
|---|---|---|---|---|---|---|---|---|---|---|---|---|---|---|---|---|
| ACT | TAC | ATG | ATT | AAC | TTG | GCA | ATG | TCA | GAC | TTG | CTT | TTT | GTT | TTT | ACT | 367 |
| Thr | Tyr | Met | Ile | Asn | Leu | Ala | Met | Ser | Asp | Leu | Leu | Phe | Val | Phe | Thr | |
| | 55 | | | | 60 | | | | | 65 | | | | | | |
| TTA | CCC | TTC | AGG | ATT | TTT | TAC | TTC | ACA | ACA | CGG | AAT | TGG | CCA | TTT | GGA | 415 |
| Leu | Pro | Phe | Arg | Ile | Phe | Tyr | Phe | Thr | Thr | Arg | Asn | Trp | Pro | Phe | Gly | |
| 70 | | | | | 75 | | | | | 80 | | | | | 85 | |
| GAT | TTA | CTT | TGT | AAG | ATT | TCT | GTG | ATG | CTG | TTT | TAT | ACC | AAC | ATG | TAC | 463 |
| Asp | Leu | Leu | Cys | Lys | Ile | Ser | Val | Met | Leu | Phe | Tyr | Thr | Asn | Met | Tyr | |
| | | | | 90 | | | | | 95 | | | | | 100 | | |
| GGA | AGC | ATT | CTG | TTC | TTA | ACC | TGT | ATT | AGT | GTA | GAT | CGA | TTT | CTG | GCA | 511 |
| Gly | Ser | Ile | Leu | Phe | Leu | Thr | Cys | Ile | Ser | Val | Asp | Arg | Phe | Leu | Ala | |
| | | 105 | | | | | 110 | | | | | 115 | | | | |
| ATT | GTC | TAC | CCA | TTT | AAG | TCA | AAG | ACT | CTA | AGA | ACC | AAA | AGA | AAT | GCA | 559 |
| Ile | Val | Tyr | Pro | Phe | Lys | Ser | Lys | Thr | Leu | Arg | Thr | Lys | Arg | Asn | Ala | |
| | 120 | | | | | 125 | | | | | 130 | | | | | |
| AAG | ATT | GTT | TGC | ACT | GGC | GTG | TGG | TTA | ACT | GTG | ATC | GGA | GGA | AGT | GCA | 607 |
| Lys | Ile | Val | Cys | Thr | Gly | Val | Trp | Leu | Thr | Val | Ile | Gly | Gly | Ser | Ala | |
| 135 | | | | | 140 | | | | | 145 | | | | | | |
| CCC | GCC | GTT | TTT | GTT | CAG | TCT | ACC | CAC | TCT | CAG | GGT | AAC | AAT | GCC | TCA | 655 |
| Pro | Ala | Val | Phe | Val | Gln | Ser | Thr | His | Ser | Gln | Gly | Asn | Asn | Ala | Ser | |
| 150 | | | | | 155 | | | | | 160 | | | | | 165 | |
| GAA | GCC | TGC | TTT | GAA | AAT | TTT | CCA | GAA | GCC | ACA | TGG | AAA | ACA | TAT | CTC | 703 |
| Glu | Ala | Cys | Phe | Glu | Asn | Phe | Pro | Glu | Ala | Thr | Trp | Lys | Thr | Tyr | Leu | |
| | | | | 170 | | | | | 175 | | | | | 180 | | |
| TCA | AGG | ATT | GTA | ATT | TTC | ATC | GAA | ATA | GTG | GGA | TTT | TTT | ATT | CCT | CTA | 751 |
| Ser | Arg | Ile | Val | Ile | Phe | Ile | Glu | Ile | Val | Gly | Phe | Phe | Ile | Pro | Leu | |
| | | | | 185 | | | | | 190 | | | | | 195 | | |
| ATT | TTA | AAT | GTA | ACT | TGT | TCT | AGT | ATG | GTG | CTA | AAA | ACT | TTA | ACC | AAA | 799 |
| Ile | Leu | Asn | Val | Thr | Cys | Ser | Ser | Met | Val | Leu | Lys | Thr | Leu | Thr | Lys | |
| | | 200 | | | | | 205 | | | | | 210 | | | | |
| CCT | GTT | ACA | TTA | AGT | AGA | AGC | AAA | ATA | AAC | AAA | ACT | AAG | GTT | TTA | AAA | 847 |
| Pro | Val | Thr | Leu | Ser | Arg | Ser | Lys | Ile | Asn | Lys | Thr | Lys | Val | Leu | Lys | |
| | 215 | | | | | 220 | | | | | 225 | | | | | |
| ATG | ATT | TTT | GTA | CAT | TTG | ATC | ATA | TTC | TGT | TTC | TGT | TTT | GTT | CCT | TAC | 895 |
| Met | Ile | Phe | Val | His | Leu | Ile | Ile | Phe | Cys | Phe | Cys | Phe | Val | Pro | Tyr | |
| 230 | | | | | 235 | | | | | 240 | | | | | 245 | |
| AAT | ATC | AAT | CTT | ATT | TTA | TAT | TCT | CTT | GTG | AGA | ACA | CAA | ACA | TTT | GTT | 943 |
| Asn | Ile | Asn | Leu | Ile | Leu | Tyr | Ser | Leu | Val | Arg | Thr | Gln | Thr | Phe | Val | |
| | | | | 250 | | | | | 255 | | | | | 260 | | |
| AAT | TGC | TCA | GTA | GTG | GCA | GCA | GTA | AGG | ACA | ATG | TAC | CCA | ATC | ACT | CTC | 991 |
| Asn | Cys | Ser | Val | Val | Ala | Ala | Val | Arg | Thr | Met | Tyr | Pro | Ile | Thr | Leu | |
| | | | 265 | | | | | 270 | | | | | 275 | | | |
| TGT | ATT | GCT | GTT | TCC | AAC | TGT | TGT | TTT | GAC | CCT | ATA | GTT | TAC | TAC | TTT | 1039 |
| Cys | Ile | Ala | Val | Ser | Asn | Cys | Cys | Phe | Asp | Pro | Ile | Val | Tyr | Tyr | Phe | |
| | | 280 | | | | | 285 | | | | | 290 | | | | |
| ACA | TCG | GAC | ACA | ATT | CAG | AAT | TCA | ATA | AAA | ATG | AAA | AAC | TGG | TCT | GTC | 1087 |
| Thr | Ser | Asp | Thr | Ile | Gln | Asn | Ser | Ile | Lys | Met | Lys | Asn | Trp | Ser | Val | |
| | 295 | | | | | 300 | | | | | 305 | | | | | |
| AGG | AGA | AGT | GAC | TTC | AGA | TTC | TCT | GAA | GTT | CAT | GGT | GCA | GAG | AAT | TTT | 1135 |
| Arg | Arg | Ser | Asp | Phe | Arg | Phe | Ser | Glu | Val | His | Gly | Ala | Glu | Asn | Phe | |
| 310 | | | | | 315 | | | | | 320 | | | | | 325 | |
| ATT | CAG | CAT | AAC | CTA | CAG | ACC | TTA | AAA | AGT | AAG | ATA | TTT | GAC | AAT | GAA | 1183 |
| Ile | Gln | His | Asn | Leu | Gln | Thr | Leu | Lys | Ser | Lys | Ile | Phe | Asp | Asn | Glu | |
| | | | | 330 | | | | | 335 | | | | | 340 | | |

TCT GCT GCC TGA AATAAAACCA TTAGGACTCA CTGGGACAGA ACTTTCAAGT   1235
Ser Ala Ala

TCCTTCAACT GTGAAAAGTG TCTTTTTGGA CAAACTATTT TTCCACCTCC AAAAGAAATT   1295

AACACA   1301

(2) INFORMATION FOR SEQ ID NO:8:

(i) SEQUENCE CHARACTERISTICS:
        (A) LENGTH: 344 amino acids
        (B) TYPE: amino acid
        (D) TOPOLOGY: linear (ii) MOLECULE TYPE: protein (xi) SEQUENCE DESCRIPTION: SEQ ID NO:8:

```
Met Val Ser Val Asn Ser Ser His Cys Phe Tyr Asn Asp Ser Phe Lys
 1               5                  10                  15
Tyr Thr Leu Tyr Gly Cys Met Phe Ser Met Val Phe Val Leu Gly Leu
            20                  25                  30
Ile Ser Asn Cys Val Ala Ile Tyr Ile Phe Ile Cys Val Leu Lys Val
        35                  40                  45
Arg Asn Glu Thr Thr Thr Tyr Met Ile Asn Leu Ala Met Ser Asp Leu
50                  55                  60
Leu Phe Val Phe Thr Leu Pro Phe Arg Ile Phe Tyr Phe Thr Thr Arg
65                  70                  75                  80
Asn Trp Pro Phe Gly Asp Leu Leu Cys Lys Ile Ser Val Met Leu Phe
                85                  90                  95
Tyr Thr Asn Met Tyr Gly Ser Ile Leu Phe Leu Thr Cys Ile Ser Val
            100                 105                 110
Asp Arg Phe Leu Ala Ile Val Tyr Pro Phe Lys Ser Lys Thr Leu Arg
        115                 120                 125
Thr Lys Arg Asn Ala Lys Ile Val Cys Thr Gly Val Trp Leu Thr Val
130                 135                 140
Ile Gly Gly Ser Ala Pro Ala Val Phe Val Gln Ser Thr His Ser Gln
145                 150                 155                 160
Gly Asn Asn Ala Ser Glu Ala Cys Phe Glu Asn Phe Pro Glu Ala Thr
                165                 170                 175
Trp Lys Thr Tyr Leu Ser Arg Ile Val Ile Phe Ile Glu Ile Val Gly
            180                 185                 190
Phe Phe Ile Pro Leu Ile Leu Asn Val Thr Cys Ser Ser Met Val Leu
        195                 200                 205
Lys Thr Leu Thr Lys Pro Val Thr Leu Ser Arg Ser Lys Ile Asn Lys
210                 215                 220
Thr Lys Val Leu Lys Met Ile Phe Val His Leu Ile Ile Phe Cys Phe
225                 230                 235                 240
Cys Phe Val Pro Tyr Asn Ile Asn Leu Ile Leu Tyr Ser Leu Val Arg
                245                 250                 255
Thr Gln Thr Phe Val Asn Cys Ser Val Val Ala Ala Val Arg Thr Met
            260                 265                 270
Tyr Pro Ile Thr Leu Cys Ile Ala Val Ser Asn Cys Cys Phe Asp Pro
        275                 280                 285
Ile Val Tyr Tyr Phe Thr Ser Asp Thr Ile Gln Asn Ser Ile Lys Met
290                 295                 300
Lys Asn Trp Ser Val Arg Arg Ser Asp Phe Arg Phe Ser Glu Val His
305                 310                 315                 320
Gly Ala Glu Asn Phe Ile Gln His Asn Leu Gln Thr Leu Lys Ser Lys
                325                 330                 335
Ile Phe Asp Asn Glu Ser Ala Ala
            340
```

(2) INFORMATION FOR SEQ ID NO:9:

(i) SEQUENCE CHARACTERISTICS:
    (A) LENGTH: 30 BASE PAIRS
    (B) TYPE: NUCLEIC ACID
    (C) STRANDEDNESS: SINGLE
    (D) TOPOLOGY: LINEAR (ii) MOLECULE TYPE: Oligonucleotide (xi) SEQUENCE DESCRIPTION: SEQ ID NO:9:

GACTAAAGCT TAATGAGTAG TGAAATGGTG                                              30

(2) INFORMATION FOR SEQ ID NO:10:

(i) SEQUENCE CHARACTERISTICS:
        (A) LENGTH: 31 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:10:

GAACTTCTAG ACCCTCAGGG TTGTAAATCA G                                            31

(2) INFORMATION FOR SEQ ID NO:11:

(i) SEQUENCE CHARACTERISTICS:
        (A) LENGTH: 30 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:11:

GACTAAAGCT TAATGAGGCC CACATGGGCA                                              30

(2) INFORMATION FOR SEQ ID NO:12:

(i) SEQUENCE CHARACTERISTICS:
        (A) LENGTH: 32 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:12:

GAACTTCTAG ACGAACTAGT GGATCCCCCC GG                                           32

(2) INFORMATION FOR SEQ ID NO:13:

(i) SEQUENCE CHARACTERISTICS:
        (A) LENGTH: 30 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:13:

GACTAAAGCT TAATGGCGTC TTTCTCTGCT                                              30

(2) INFORMATION FOR SEQ ID NO:14:

(i) SEQUENCE CHARACTERISTICS:
        (A) LENGTH: 30 BASE PAIRS
        (B) TYPE: NUCLEIC ACID
        (C) STRANDEDNESS: SINGLE
        (D) TOPOLOGY: LINEAR (ii) MOLECULE TYPE:  Oligonucleotide (xi) SEQUENCE DESCRIPTION:  SEQ ID NO:14:

GAACTTCTAG ACTTCACACA GTTGTACTAT                              30

(2) INFORMATION FOR SEQ ID NO:15:

(i) SEQUENCE CHARACTERISTICS:
            (A) LENGTH:  30 BASE PAIRS
            (B) TYPE:  NUCLEIC ACID
            (C) STRANDEDNESS:  SINGLE
            (D) TOPOLOGY:  LINEAR (ii) MOLECULE TYPE:  Oligonucleotide (xi) SEQUENCE DESCRIPTION:  SEQ ID NO:15:

GACTAAAGCT TAATGGTAAG CGTTAACAGC                              30

(2) INFORMATION FOR SEQ ID NO:16:

(i) SEQUENCE CHARACTERISTICS:
            (A) LENGTH:  31 BASE PAIRS
            (B) TYPE:  NUCLEIC ACID
            (C) STRANDEDNESS:  SINGLE
            (D) TOPOLOGY:  LINEAR (ii) MOLECULE TYPE:  Oligonucleotide (xi) SEQUENCE DESCRIPTION:  SEQ ID NO:16:

GAACTTCTAG ACTTCAGGCA GCAGATTCAT T                            31

(2) INFORMATION FOR SEQ ID NO:17:

(i) SEQUENCE CHARACTERISTICS:
            (A) LENGTH:  34 BASE PAIRS
            (B) TYPE:  NUCLEIC ACID
            (C) STRANDEDNESS:  SINGLE
            (D) TOPOLOGY:  LINEAR (ii) MOLECULE TYPE:  Oligonucleotide (xi) SEQUENCE DESCRIPTION:  SEQ ID NO:17:

GTCCAAGCTT GCCACCATGA GTAGTGAAAT GGTG                         34

(2) INFORMATION FOR SEQ ID NO:18:

(i) SEQUENCE CHARACTERISTICS:
            (A) LENGTH:  58 BASE PAIRS
            (B) TYPE:  NUCLEIC ACID
            (C) STRANDEDNESS:  SINGLE
            (D) TOPOLOGY:  LINEAR (ii) MOLECULE TYPE:  Oligonucleotide (xi) SEQUENCE DESCRIPTION:  SEQ ID NO:18:

CTAGCTCGAG TCAAGCGTAG TCTGGGACGT CGTATGGGTA GCAGGGTTGT AAATCAGG     58

(2) INFORMATION FOR SEQ ID NO:19:

(i) SEQUENCE CHARACTERISTICS:
            (A) LENGTH:  34 BASE PAIRS
            (B) TYPE:  NUCLEIC ACID
            (C) STRANDEDNESS:  SINGLE
            (D) TOPOLOGY:  LINEAR (ii) MOLECULE TYPE:  Oligonucleotide (xi) SEQUENCE DESCRIPTION:  SEQ ID NO:19:

```
GTCCAAGCTT GCCACCATGG TTGGTGGCAC CTGG                                    34

(2) INFORMATION FOR SEQ ID NO:20:

(i) SEQUENCE CHARACTERISTICS:
        (A) LENGTH: 58 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:20:

CTAGCTCGAG TCAAGCGTAG TCTGGGACGT CGTATGGGTA GCAGTGGATC CCCCGTGC         58

(2) INFORMATION FOR SEQ ID NO:21:

(i) SEQUENCE CHARACTERISTICS:
        (A) LENGTH: 34 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:21:

GTCCAAGCTT GCCACCATGA ACACCACAGT AATG                                    34

(2) INFORMATION FOR SEQ ID NO:22:

(i) SEQUENCE CHARACTERISTICS:
        (A) LENGTH: 61 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:22:

CTAGCTCGAG TCAAGCGTAG TCTGGGACGT CGTATGGGTA GCAAGGGATC CATACAAATG       60
T                                                                        61

(2) INFORMATION FOR SEQ ID NO:23:

(i) SEQUENCE CHARACTERISTICS:
        (A) LENGTH: 34 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:23:

GTCCAAGCTT GCCACCATGG TAAGCGTTAA CAGC                                    34

(2) INFORMATION FOR SEQ ID NO:24:

(i) SEQUENCE CHARACTERISTICS:
        (A) LENGTH: 61 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:24:

CTAGCTCGAG TCAAGCGTAG TCTGGGACGT CGTATGGGTA GCAGGCAGCA GATTCATTGT       60
C                                                                        61
```

(2) INFORMATION FOR SEQ ID NO:25:

(i) SEQUENCE CHARACTERISTICS:
        (A) LENGTH: 30 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:25:

```
CGGGATCCCT CCATGAGTAG TGAAATGGTG                                          30
```

(2) INFORMATION FOR SEQ ID NO:26:

(i) SEQUENCE CHARACTERISTICS:
        (A) LENGTH: 29 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:26:

```
CGGGATCCCG CTCAGGGTTG TAAATCAGG                                           29
```

(2) INFORMATION FOR SEQ ID NO:27:

(i) SEQUENCE CHARACTERISTICS:
        (A) LENGTH: 222 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:27:

```
Phe Phe Leu Ser His Leu Ala Ile Val Asp Ile Ala Tyr Ala Cys Asn
 1               5                  10                  15

Thr Val Pro Gln Met Leu Val Asn Leu Leu Asp Pro Val Lys Pro Ile
             20                  25                  30

Ser Tyr Ala Gly Cys Met Thr Gln Thr Phe Leu Phe Leu Thr Phe Ala
         35                  40                  45

Ile Thr Glu Cys Leu Leu Leu Val Val Met Ser Tyr Asp Arg Tyr Val
 50                  55                  60

Ala Ile Cys His Pro Leu Arg Tyr Ser Ala Ile Met Ser Trp Arg Val
 65                  70                  75                  80

Cys Ser Thr Met Ala Val Thr Ser Trp Ile Ile Gly Val Leu Leu Ser
                 85                  90                  95

Leu Ile His Leu Val Leu Leu Pro Leu Pro Phe Cys Val Ser Gln
                100                 105                 110

Lys Val Asn His Phe Phe Cys Glu Ile Thr Ala Ile Leu Lys Leu Ala
                115                 120                 125

Cys Ala Asp Thr His Leu Asn Glu Thr Met Val Leu Ala Gly Ala Val
                130                 135                 140

Ser Val Leu Val Gly Pro Phe Ser Ser Ile Val Ser Tyr Ala Cys
145                 150                 155                 160

Ile Leu Gly Ala Ile Leu Lys Ile Gln Ser Glu Gly Gln Arg Lys
                165                 170                 175

Ala Phe Ser Thr Cys Ser Ser His Leu Cys Val Val Gly Leu Phe Tyr
                180                 185                 190
```

```
Gly Thr Ala Ile Val Met Tyr Val Gly Pro Arg His Gly Ser Pro Lys
            195                 200                 205

Glu Gln Lys Lys Tyr Leu Leu Leu Phe His Ser Leu Phe Asn
210                 215                 220
```

(2) INFORMATION FOR SEQ ID NO:28:

(i) SEQUENCE CHARACTERISTICS:
      (A) LENGTH: 381 amino acids
      (B) TYPE: amino acid
      (C) STRANDEDNESS: single
      (D) TOPOLOGY: Not Relevant (ii) MOLECULE TYPE: peptide (xi) SEQUENCE DESCRIPTION: SEQ ID NO:28:

```
Met Gly Pro Thr Ser Val Pro Leu Val Lys Ala His Arg Ser Ser Val
1               5                   10                  15

Ser Asp Tyr Val Asn Tyr Asp Ile Ile Val Arg His Tyr Asn Tyr Thr
            20                  25                  30

Gly Lys Leu Asn Ile Ser Ala Asp Lys Glu Asn Ser Ile Lys Leu Thr
            35                  40                  45

Ser Val Val Phe Ile Leu Ile Cys Cys Phe Ile Ile Leu Glu Asn Ile
50                  55                  60

Phe Val Leu Leu Thr Ile Trp Lys Thr Lys Phe His Arg Pro Met
65                  70                  75                  80

Tyr Tyr Phe Ile Gly Asn Leu Ala Leu Ser Asp Leu Leu Ala Gly Val
                85                  90                  95

Ala Tyr Thr Ala Asn Leu Leu Leu Ser Gly Ala Thr Thr Tyr Lys Leu
                100                 105                 110

Thr Pro Ala Gln Trp Phe Leu Arg Glu Gly Ser Met Phe Val Ala Leu
            115                 120                 125

Ser Ala Ser Val Phe Ser Leu Leu Ala Ile Ala Ile Glu Arg Tyr Ile
            130                 135                 140

Thr Met Leu Lys Met Lys Leu His Asn Gly Ser Asn Asn Phe Arg Leu
145                 150                 155                 160

Phe Leu Leu Ile Ser Ala Cys Trp Val Ile Ser Leu Ile Leu Gly Gly
                165                 170                 175

Leu Pro Ile Met Gly Trp Asn Cys Ile Ser Ala Leu Ser Ser Cys Ser
                180                 185                 190

Thr Val Leu Pro Leu Tyr His Lys His Tyr Ile Leu Phe Cys Thr Thr
            195                 200                 205

Val Phe Thr Leu Leu Leu Leu Ser Ile Val Ile Leu Tyr Cys Arg Ile
            210                 215                 220

Tyr Ser Leu Val Arg Thr Arg Ser Arg Arg Leu Thr Phe Arg Lys Asn
225                 230                 235                 240

Ile Ser Lys Ala Ser Arg Ser Ser Glu Asn Val Ala Leu Leu Lys Thr
                245                 250                 255

Val Ile Ile Val Leu Ser Val Phe Ile Ala Cys Trp Ala Pro Leu Phe
                260                 265                 270

Ile Leu Leu Leu Leu Asp Val Gly Cys Lys Val Lys Thr Cys Asp Ile
            275                 280                 285

Leu Phe Arg Ala Glu Tyr Phe Leu Val Leu Ala Val Leu Asn Ser Gly
            290                 295                 300

Thr Asn Pro Ile Ile Tyr Thr Leu Thr Asn Lys Glu Met Arg Arg Ala
305                 310                 315                 320

Phe Ile Arg Ile Met Ser Cys Cys Lys Cys Pro Ser Gly Asp Ser Ala
```

```
                         325                 330                 335
Gly Lys Phe Lys Arg Pro Ile Ile Ala Gly Met Glu Phe Ser Arg Ser
                    340                 345                 350

Lys Ser Asp Asn Ser Ser His Pro Gln Lys Asp Glu Gly Asp Asn Pro
                355                 360                 365

Glu Thr Ile Met Ser Ser Gly Asn Val Asn Ser Ser Ser
            370                 375                 380

(2) INFORMATION FOR SEQ ID NO:29:

(i) SEQUENCE CHARACTERISTICS:
        (A) LENGTH: 325 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:29:

Ile Asn Ser Thr Ser Thr Gln Pro Pro Asp Glu Ser Cys Ser Gln Asn
1               5                  10                  15

Leu Leu Ile Thr Gln Gln Ile Ile Pro Val Leu Tyr Cys Met Val Phe
                20                  25                  30

Ile Ala Gly Ile Leu Leu Asn Gly Val Ser Gly Trp Ile Phe Phe Tyr
            35                  40                  45

Val Pro Ser Ser Lys Ser Phe Ile Ile Tyr Leu Lys Asn Ile Val Ile
        50                  55                  60

Ala Asp Phe Val Met Ser Leu Thr Phe Pro Phe Lys Ile Leu Gly Asp
65                  70                  75                  80

Ser Gly Leu Gly Pro Trp Gln Leu Asn Val Phe Val Cys Arg Val Ser
                85                  90                  95

Ala Val Leu Phe Tyr Val Asn Met Tyr Val Ser Ile Val Phe Phe Gly
                100                 105                 110

Leu Ile Ser Phe Asp Arg Tyr Tyr Lys Ile Val Lys Pro Leu Trp Thr
            115                 120                 125

Ser Phe Ile Gln Ser Val Ser Tyr Ser Lys Leu Leu Ser Val Ile Val
        130                 135                 140

Trp Met Leu Met Leu Leu Leu Ala Val Pro Asn Ile Ile Leu Thr Asn
145                 150                 155                 160

Gln Ser Val Arg Glu Val Thr Gln Ile Lys Cys Ile Glu Leu Lys Ser
                165                 170                 175

Glu Leu Gly Arg Lys Trp His Lys Ala Ser Asn Tyr Ile Phe Val Ala
                180                 185                 190

Ile Phe Trp Ile Val Phe Leu Leu Leu Ile Val Phe Tyr Thr Ala Ile
            195                 200                 205

Thr Lys Lys Ile Phe Lys Ser His Leu Lys Ser Ser Arg Asn Ser Thr
        210                 215                 220

Ser Val Lys Lys Ser Ser Arg Asn Ile Phe Ser Ile Val Phe Val
225                 230                 235                 240

Phe Phe Val Cys Phe Val Pro Tyr His Ile Ala Arg Ile Pro Tyr Thr
                245                 250                 255

Lys Ser Gln Thr Glu Ala His Tyr Ser Cys Gln Ser Lys Glu Ile Leu
                260                 265                 270

Arg Tyr Met Lys Glu Phe Thr Leu Leu Leu Ser Ala Ala Asn Val Cys
            275                 280                 285

Leu Asp Pro Ile Ile Tyr Phe Phe Leu Cys Gln Pro Phe Arg Glu Ile
        290                 295                 300
```

```
Leu Cys Lys Lys Leu His Ile Pro Leu Lys Ala Gln Asn Asp Leu Asp
305                 310                 315                 320

Ile Ser Arg Ile Lys
                325
```

(2) INFORMATION FOR SEQ ID NO:30:

(i) SEQUENCE CHARACTERISTICS:
        (A) LENGTH: 302 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:30:

```
Ser Ser Asn Cys Ser Thr Glu Asp Ser Phe Lys Tyr Thr Leu Tyr Gly
1               5                   10                  15

Cys Val Phe Ser Met Val Phe Val Leu Gly Leu Ile Ala Asn Cys Val
                20                  25                  30

Ala Ile Tyr Ile Phe Thr Phe Thr Leu Lys Val Arg Asn Glu Thr Thr
                35                  40                  45

Thr Tyr Met Leu Met Leu Ala Ile Ser Asp Leu Leu Phe Val Phe Thr
50                  55                  60

Leu Pro Phe Arg Ile Tyr Tyr Phe Val Val Arg Asn Trp Pro Phe Gly
65                  70                  75                  80

Asp Val Leu Cys Lys Ile Ser Val Thr Leu Phe Tyr Thr Asn Met Tyr
                85                  90                  95

Gly Ser Ile Leu Phe Leu Thr Cys Ile Ser Val Asp Arg Phe Leu Ala
                100                 105                 110

Ile Val His Pro Phe Arg Ser Lys Thr Leu Arg Thr Lys Arg Asn Ala
                115                 120                 125

Arg Ile Val Cys Val Ala Val Trp Ile Thr Val Leu Ala Gly Ser Thr
130                 135                 140

Pro Ala Ser Phe Phe Gln Ser Thr Asn Arg Gln Asn Asn Thr Glu Gln
145                 150                 155                 160

Arg Thr Cys Phe Glu Asn Phe Pro Glu Ser Thr Trp Lys Thr Tyr Leu
                165                 170                 175

Ser Arg Ile Val Ile Phe Ile Glu Ile Val Gly Phe Phe Ile Pro Leu
                180                 185                 190

Ile Leu Asn Val Thr Cys Ser Thr Met Val Leu Arg Thr Leu Asn Lys
                195                 200                 205

Pro Leu Thr Leu Ser Arg Asn Lys Leu Ser Lys Lys Val Leu Lys
210                 215                 220

Met Ile Phe Val His Leu Val Ile Phe Cys Phe Cys Phe Val Pro Tyr
225                 230                 235                 240

Asn Ile Thr Leu Ile Leu Tyr Ser Leu Met Arg Thr Gln Thr Trp Ile
                245                 250                 255

Asn Cys Ser Val Val Thr Ala Val Arg Thr Met Tyr Pro Val Thr Leu
                260                 265                 270

Cys Ile Ala Val Ser Asn Cys Cys Phe Asp Pro Ile Val Tyr Tyr Phe
                275                 280                 285

Thr Ser Asp Thr Asn Ser Glu Leu Asp Lys Lys Gln Gln Val
290                 295                 300
```